United States Patent
Coulthard et al.

(10) Patent No.: US 8,579,872 B2
(45) Date of Patent: Nov. 12, 2013

(54) REDUCED-PRESSURE SYSTEMS, DRESSINGS, AND METHODS EMPLOYING A WIRELESS PUMP

(75) Inventors: Richard Daniel John Coulthard, Verwood (GB); Christopher Brian Locke, Bournemouth (GB); Benjamin Stokes, Ringwood (GB)

(73) Assignee: KCI Licensing, Inc., San Antonio, TX (US)

( * ) Notice: Subject to any disclaimer, the term of this patent is extended or adjusted under 35 U.S.C. 154(b) by 98 days.

(21) Appl. No.: 13/183,136

(22) Filed: Jul. 14, 2011

(65) Prior Publication Data
US 2012/0109083 A1 May 3, 2012

Related U.S. Application Data

(60) Provisional application No. 61/407,194, filed on Oct. 27, 2010, provisional application No. 61/418,730, filed on Dec. 1, 2010, provisional application No. 61/445,383, filed on Feb. 22, 2011, provisional application No. 61/445,338, filed on Feb. 22, 2011.

(51) Int. Cl.
*A61M 1/00* (2006.01)

(52) U.S. Cl.
USPC .......................................... 604/319; 604/317

(58) Field of Classification Search
USPC .................... 604/319, 317; 602/42
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

International Search Report and Written Opinion date mailed Oct. 24, 2011; PCT International Application No. PCT/US2011/044187.

(Continued)

*Primary Examiner* — Loan Thanh
*Assistant Examiner* — Andrew S Lo

(57) ABSTRACT

Systems, methods, and dressings for providing reduced pressure to a tissue site on a patient are presented that involve wirelessly providing power to a reduced-pressure pump. In one instance, a RFID antenna is used to power a reduced-pressure pump that is fluidly coupled by a conduit to a reduced-pressure dressing. In another instance, a reduced-pressure dressing incorporates a micro-pump and a RFID antenna that is used to power the micro-pump. Other systems, methods, and devices are presented.

17 Claims, 12 Drawing Sheets

(56) References Cited

U.S. PATENT DOCUMENTS

| | | |
|---|---|---|
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,191,013 B1 | 3/2007 | Miranda et al. |
| 7,569,742 B2 | 8/2009 | Haggstrom et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2007/0078366 A1* | 4/2007 | Haggstrom et al. ............ 602/53 |
| 2008/0082059 A1* | 4/2008 | Fink et al. ..................... 604/305 |
| 2009/0005727 A1* | 1/2009 | Hood et al. ..................... 604/65 |
| 2009/0227969 A1* | 9/2009 | Jaeb et al. ..................... 604/313 |
| 2009/0240185 A1 | 9/2009 | Jaeb et al. |
| 2011/0112492 A1* | 5/2011 | Bharti et al. ................... 604/319 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| KR | 2002 0032508 A | 5/2002 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 2008/051924 A2 | 5/2008 |

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

(56) References Cited

OTHER PUBLICATIONS

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Đukić, Ž. Maksimović, Đ.. Radak, and P. Peška, "Vacuum Therapy in the Treatment of Peripheral Blood Vessels," *Timok Medical Journal* 11 (1986), pp. 161-164 (certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Gonstruction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

Nikitin, et al "Performance Limitations of Passive UHF RFID Systems" IEEE, 2006, 1011-1014.

\* cited by examiner

REDUCED-PRESSURE SYSTEMS, DRESSINGS, AND METHODS EMPLOYING A WIRELESS PUMP

RELATED APPLICATION

The present invention claims the benefit, under 35 USC §119(e), of the filing of U.S. Provisional Patent Application Ser. No. 61/407,194, entitled "System and Methods For Electrically Detecting The Presence of Exudate In Reduced-Pressure Dressings," filed 27 Oct. 2010, which is incorporated herein by reference for all purposes [VAC.0975PRO1]; U.S. Provisional Patent Application Ser. No. 61/418,730, entitled "Systems and Methods for Electrically Detecting the Presence of Exudate in Dressings," filed 1 Dec. 2010, which is incorporated herein by reference for all purposes [VAC.0975PRO2]; U.S. Provisional Patent Application Ser. No. 61/445,383, entitled "Interactive, Wireless Reduced-Pressure Dressings, Methods, and Systems," filed 22 Feb. 2011, which is incorporated herein by reference for all purposes [VAC.0999PRO]; and U.S. Provisional Patent Application Ser. No. 61/445,338, entitled "Reduced-Pressure Systems, Dressings, and Methods Employing a Wireless Pump," filed 22 Feb. 2011, which is incorporated herein by reference for all purposes [VAC.1000PRO].

FIELD

The present disclosure relates generally to medical treatment systems and, more particularly, but not by way of limitation, to systems, dressings, and methods that involve wirelessly providing power to a pump that applies reduced pressure to a tissue site.

BACKGROUND

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, when applied to open wounds, reduced pressure is applied to tissue through a porous pad or other manifold device. The porous pad distributes reduced pressure to the tissue and channels fluids that are drawn from the tissue. Reduced pressure may also be used to remove fluids from a body cavity, such as an abdominal cavity.

SUMMARY

According to an illustrative embodiment, a system for treating a tissue site with reduced pressure includes a reduced-pressure dressing for disposing proximate to the tissue site and a wireless, reduced-pressure pump fluidly coupled to the reduced-pressure dressing. The wireless, reduced-pressure pump includes a Radio Frequency Identification (RFID) antenna, a first processor coupled to the RFID antenna, a micro-pump device coupled to the processor for receiving power and developing reduced pressure, a first pump-sealing member, a fluid reservoir, and a second pump-sealing member. The first pump-sealing member and second pump sealing are at least partially coupled to form a pump pouch in which the micro-pump is disposed. The system further includes a base unit having a RFID reader. The RFID reader is configured to provide power to the RFID antenna such that the micro-pump is powered.

According to another illustrative embodiment, a method of manufacturing a system for treating a tissue site on a patient with reduced pressure includes providing a reduced-pressure dressing for disposing proximate to the tissue site and providing a wireless, reduced pressure pump. The wireless, reduced-pressure pump includes a RFID antenna, a first processor coupled to the RFID antenna, a micro-pump device coupled to the first processor for receiving power and developing a reduced pressure, a first pump-sealing member, a fluid reservoir, and a second pump-sealing member. The first pump-sealing member and second pump sealing are at least partially coupled to form a pump pouch in which the micro-pump is disposed. The method may further include providing a reduced-pressure delivery conduit for fluidly coupling the wireless, reduced-pressure pump to the reduced-pressure dressing. The method further includes providing a base unit having a RFID reader. The RFID reader is configured to provide power to the RFID antenna such that the micro-pump is powered.

According to another illustrative embodiment, a method for treating a tissue site on a patient with reduced pressure includes placing a reduced-pressure dressing proximate to the tissue site and providing a wireless, reduced-pressure pump. The wireless, reduced-pressure pump includes a RFID antenna, a first processor coupled to the RFID antenna, a micro-pump device coupled to the processor for receiving power and developing reduced pressure, a first pump-sealing member, a fluid reservoir, and a second pump-sealing member. The first pump-sealing member and second pump sealing are at least partially coupled to form a pump pouch in which the micro-pump is disposed. The method further includes fluidly coupling the wireless, reduced-pressure pump to the reduced-pressure dressing, providing a base unit having a RFID reader and a second processor, and activating the base unit whereby the RFID reader and second processor transmit an activation signal to the wireless, reduced-pressure pump to activate the wireless, reduced-pressure pump.

According to another illustrative embodiment, a reduced-pressure system for treating a tissue site with reduced pressure includes a reduced-pressure dressing. The reduced-pressure dressing includes a first distribution manifold for placing proximate to the tissue site, an absorbent layer for receiving and retaining fluids from the first distribution manifold, a RFID antenna, a first processor coupled to the RFID antenna, and a micro-pump coupled to the first processor for receiving power therefrom and developing reduced pressure. The micro-pump has an inlet and an exhaust outlet. The system also includes a first sealing member for forming a sealed space over the tissue site and the micro-pump, and a vent fluidly coupling the exhaust outlet of the micro-pump to an exterior. The system further includes a base unit that includes a RFID reader. The base unit is operable to supply a pump signal to the reduced-pressure dressing to energize the micro-pump.

According to another illustrative embodiment, a method for treating a tissue site on a patient with reduced pressure includes disposing a wireless, reduced-pressure dressing proximate to the tissue site. The wireless, reduced-pressure dressing includes a first distribution manifold for placing proximate to the tissue site, an absorbent layer for receiving and retaining fluids from the first distribution manifold, a RFID antenna, a first processor coupled to the RFID antenna, a micro-pump coupled to the first processor for receiving power therefrom and developing reduced pressure. The micro-pump has an inlet and an exhaust outlet, a first sealing member for forming a sealed space over the tissue site and the micro-pump, and a vent fluidly coupling the exhaust outlet of the micro-pump to an exterior. The method further includes providing a base unit comprising a RFID reader. The base unit is operable to supply a pump signal to the wireless, reduced-pressure dressing to energize the micro-pump. The method also includes activating the base unit to deliver the pump signal to the wireless, reduced-pressure dressing.

Other features and advantages of the illustrative embodiments will become apparent with reference to the drawings and detailed description that follow.

DETAILED DESCRIPTION OF ILLUSTRATIVE EMBODIMENTS

Figure 1:
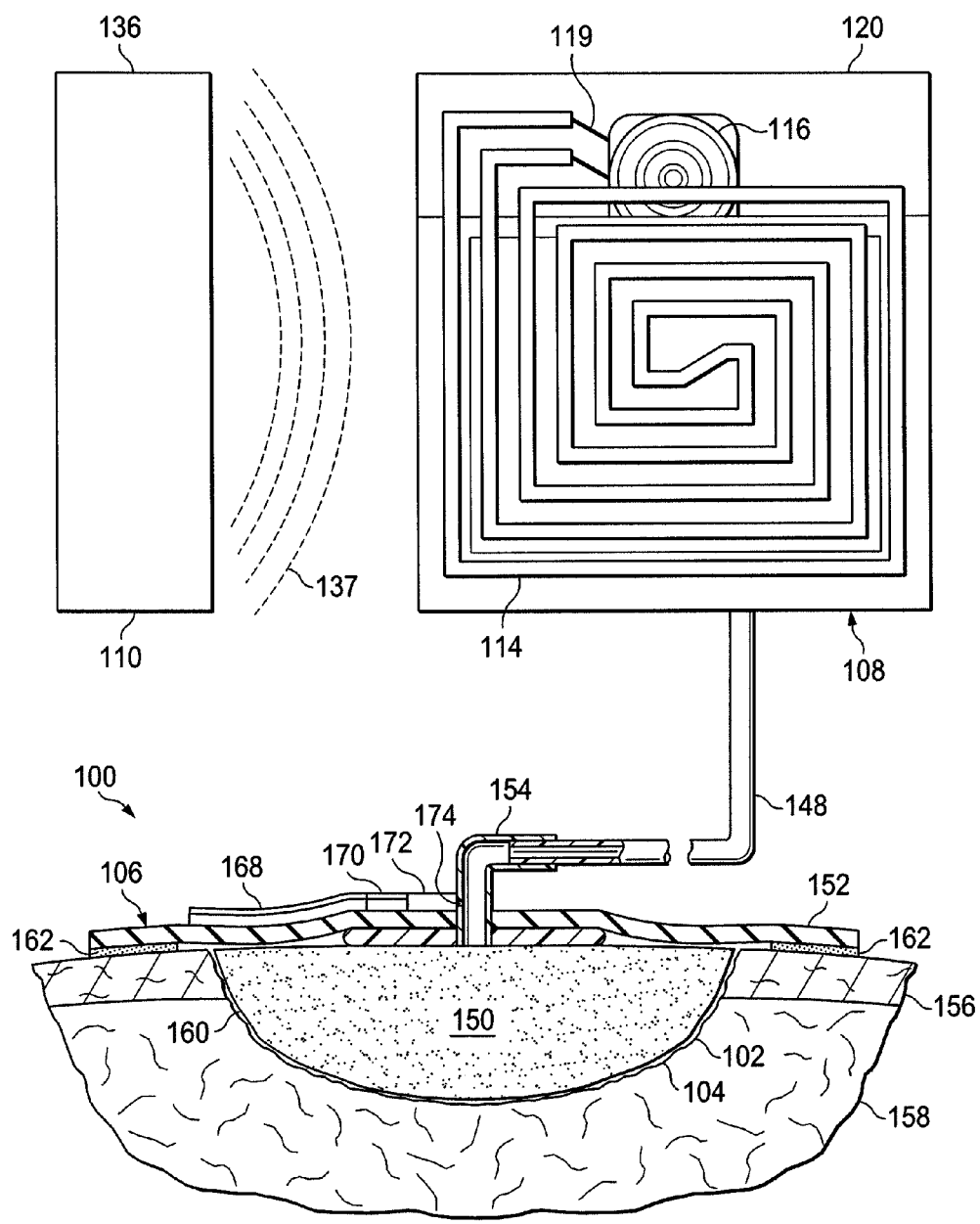
FIG. 1 is a schematic diagram, with a portion shown in cross section, of an illustrative embodiment of a system for treating a tissue site with reduced pressure.

In the following detailed description of the illustrative, non-limiting embodiments, reference is made to the accompanying drawings that form a part hereof. These illustrative embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments is defined only by the appended claims.

The illustrative embodiments herein involve using Radio Frequency Identification (RFID) or an enhanced type of Radio Frequency Identification (RFID) technology to energize a micro-pump device in a reduced-pressure dressing. RFID traditionally uses a RFID tag or label that is on a target and a RFID reader that energizes and reads signals from the RFID tag. One common example is a toll tag. Most RFID tags include an integrated circuit for storing and processing information, a modulator, and demodulator. RFID tags can be passive tags, active RFID tags, and battery-assisted passive tags. Generally, passive tags use no battery and do not transmit information unless they are energized by a RFID reader. Active tags have an on-board battery and can transmit autonomously (i.e., without being energized by a RFID reader). Battery-assisted passive tags typically have a small battery on-board that is activated in the presence of a RFID reader. To enhance the RFID tag, a microcontroller and sensor may be incorporated into the reduced-pressure dressing. The RFID tag, a microcontroller and sensor allow sensing and optional computational functions. Moreover, the RFID tag and microcontroller partially or entirely power a micro-pump.

In one illustrative embodiment, the enhanced RFID technology is a Wireless Identification and Sensing Platform (WISP) device. WISPs involve powering and reading a WISP device, analogous to a RFID tag (or label), with a RFID reader. The WISP device harvests the power from the RFID reader's emitted radio signals and performs sensing functions (and optionally performs computational functions). The WISP device transmits a radio signal with information to the RFID reader. The WISP device receives power from the RFID reader. The WISP device has a tag or antenna, that harvests energy and a microcontroller (or processor) that can perform a variety of tasks, such as sampling sensors. The WISP device reports data to the RFID reader. In one illustrative embodiment, the WISP device includes an integrated circuit with power harvesting circuitry, demodulator, modulator, microcontroller, sensors, and may include one or more capacitors for storing energy. A form of WISP technology has been developed by Intel Research Seattle. RFID devices as used herein also include WISP devices.

Referring now to the drawings and initially to FIGS. 1-5, an illustrative embodiment of a system 100 for treating a tissue site 102, e.g., a wound 104 or a cavity, with reduced pressure is presented. The system 100 includes a reduced-pressure dressing 106 for disposing proximate to the tissue site 102; a wireless, reduced-pressure pump 108 fluidly coupled to the reduced-pressure dressing 106; and a base unit 110 having a RFID reader 112. The wireless, reduced-pressure pump 108 includes a first RFID antenna 114 and a micro-pump device 116. The RFID reader 112 is configured to provide and transmit a pump signal that provides power to the first RFID antenna 114. The pump signal received by the first RFID antenna 114 powers the micro-pump device 116. Remotely powering the micro-pump device 116 provides a number of potential benefits. The benefits may include ease of application. In addition, the wireless, reduced-pressure pump 108 may be a self-contained, disposable unit. It should be noted that some variation is shown between figures in order to show some of the potential variations in the illustrative system 100.

The system 100 may be used with various different types of tissue sites 102. The tissue site 102 may be the bodily tissue of any human, animal, or other organism, including bone tissue, adipose tissue, muscle tissue, dermal tissue, vascular tissue, connective tissue, cartilage, tendons, ligaments, body cavity or any other tissue. Treatment of the tissue site 102 may include removal of fluids, e.g., exudate or ascites.

The wireless, reduced-pressure pump 108 includes the first RFID antenna 114 that is coupled to a first processor 118 by electrical leads 119. The first processor 118 is coupled to the micro-pump device 116, or micro-pump, for receiving power. The first processor 118 may be incorporated into the micro-pump device 116. The first processor 118 and micro-pump device 116 may be located within a pump pouch 120.

The pump pouch 120 may be formed by coupling a first pump-sealing member 122 to a second pump-sealing member 124. The pump pouch 120 may also be formed by other techniques such as casting the pump pouch 120 from a polymer. At least a portion of the pump pouch 120 comprises a fluid reservoir 126 for receiving and retaining fluids 127 from the tissue site 102. The micro-pump device 116 may be a piezoelectric pump, a peristaltic pump, or other small pump that produces reduced pressure with minimal power requirements. The first processor 118 is operable to receive a pressure message signal from a pressure sensing device 138. In response to receiving the pressure message signal, the first processor 118 produces a control signal to activate or deactivate the micro-pump device 116. The pressure sensing device 138 may be a transducer or may be a simple switch that is activated if sufficient reduced pressure is present.

Figure 3:
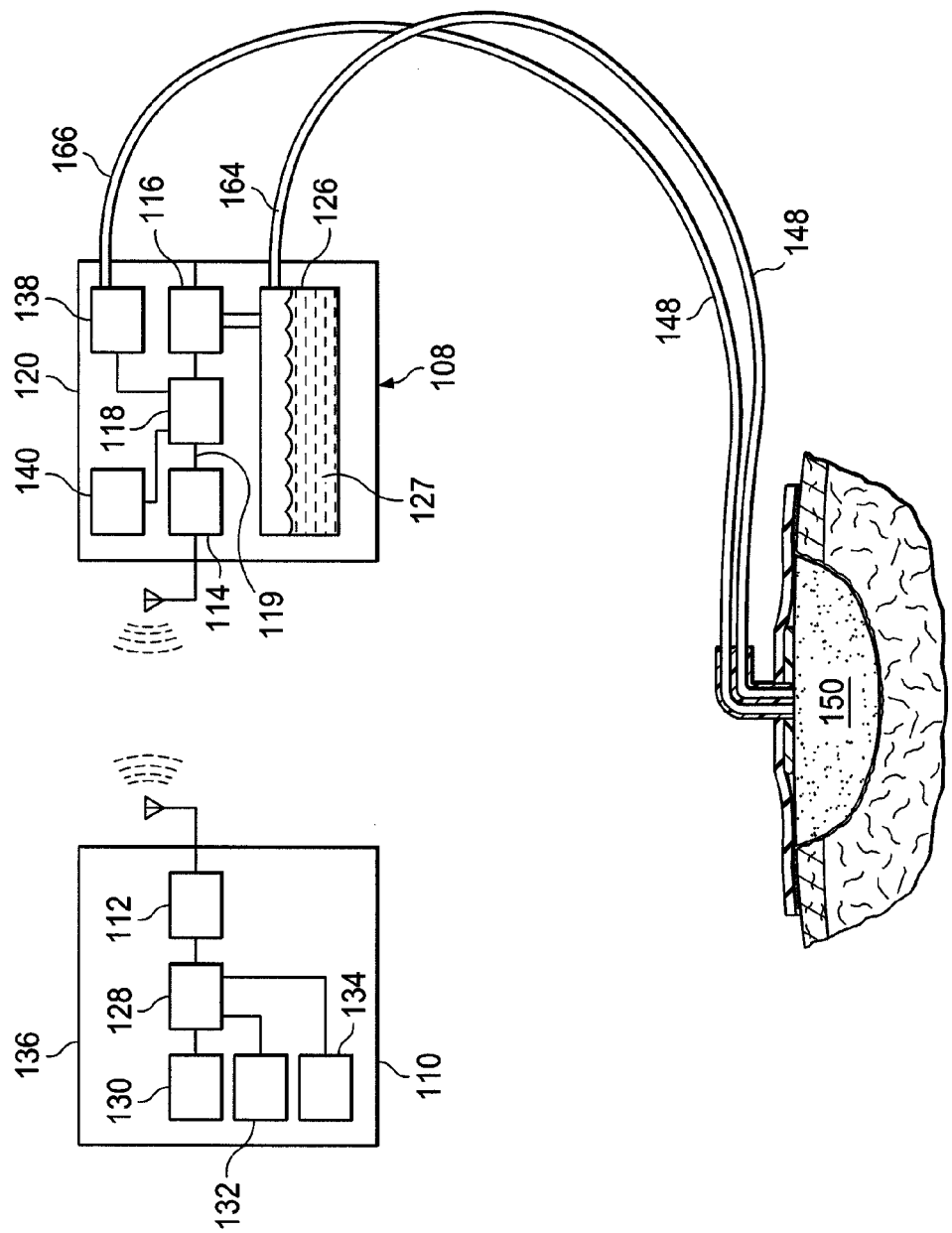
FIG. 3 is a schematic diagram, with a portion shown in cross section, of the system of FIG. 1 presenting additional aspects and some alternatives.

Referring primarily to FIG. 3, the base unit 110 includes a second processor 128 coupled to the RFID reader 112. A control panel 130 (e.g., a user interface), a first display 132 and a power source 134 (e.g., a battery or electrical connection) may also be coupled to the second processor 128. The base unit 110 may include a base housing 136. The second processor 128 and RFID reader 112 are configured to transmit a signal 137, e.g., a pump signal or a pressure inquiry signal, to the first RFID antenna 114.

The first RFID antenna 114 of the reduced-pressure pump 108 is coupled by electrical leads 119 or a wireless coupling to the first processor 118. The first processor 118 is coupled to the micro-pump device 116 to provide power and control the micro-pump device 116. A first power source 140 may be included to provide additional power to the first processor 118. A pressure sensing device 138 may be coupled to the first processor 118. The pressure sensing device 138 is fluidly coupled to and senses pressure in a pressure sensing lumen 166 (or vent passageway 174 or interface distribution manifold 150). The micro-pump device 116 is fluidly coupled to a fluid reservoir 126. The fluid reservoir 126 receives and retains the fluids 127 from a reduced-pressure lumen 164 or from the interface distribution manifold 150.

The pump signal transmitted by the base unit 110 is received by the first RFID antenna 114 and energizes the micro-pump device 116 to produce reduced pressure. The pressure inquiry signal is transmitted to the first processor 118 of the wireless, reduced-pressure pump 108 by the second processor 128 and RFID reader 112. In response, the first processor 118 and pressure sensing device 138 of the wireless, reduced-pressure pump 108 transmit a pressure message signal indicative of the pressure experienced at the reduced-pressure dressing 106 to the base unit 110.

The second processor 128 is configured to receive the pressure message signal from the wireless, reduced-pressure pump 108 and prepare a control signal. The second processor 128 and RFID reader 112 are configured to transmit the control signal to the wireless, reduced-pressure pump 108 to activate or deactivate the micro-pump device 116. In another illustrative embodiment, as previously mentioned, the first processor 118 is operable to receive a pressure message signal from the pressure sensing device 138 and to produce a control signal to activate or deactivate the micro-pump device 116.

Figure 2:
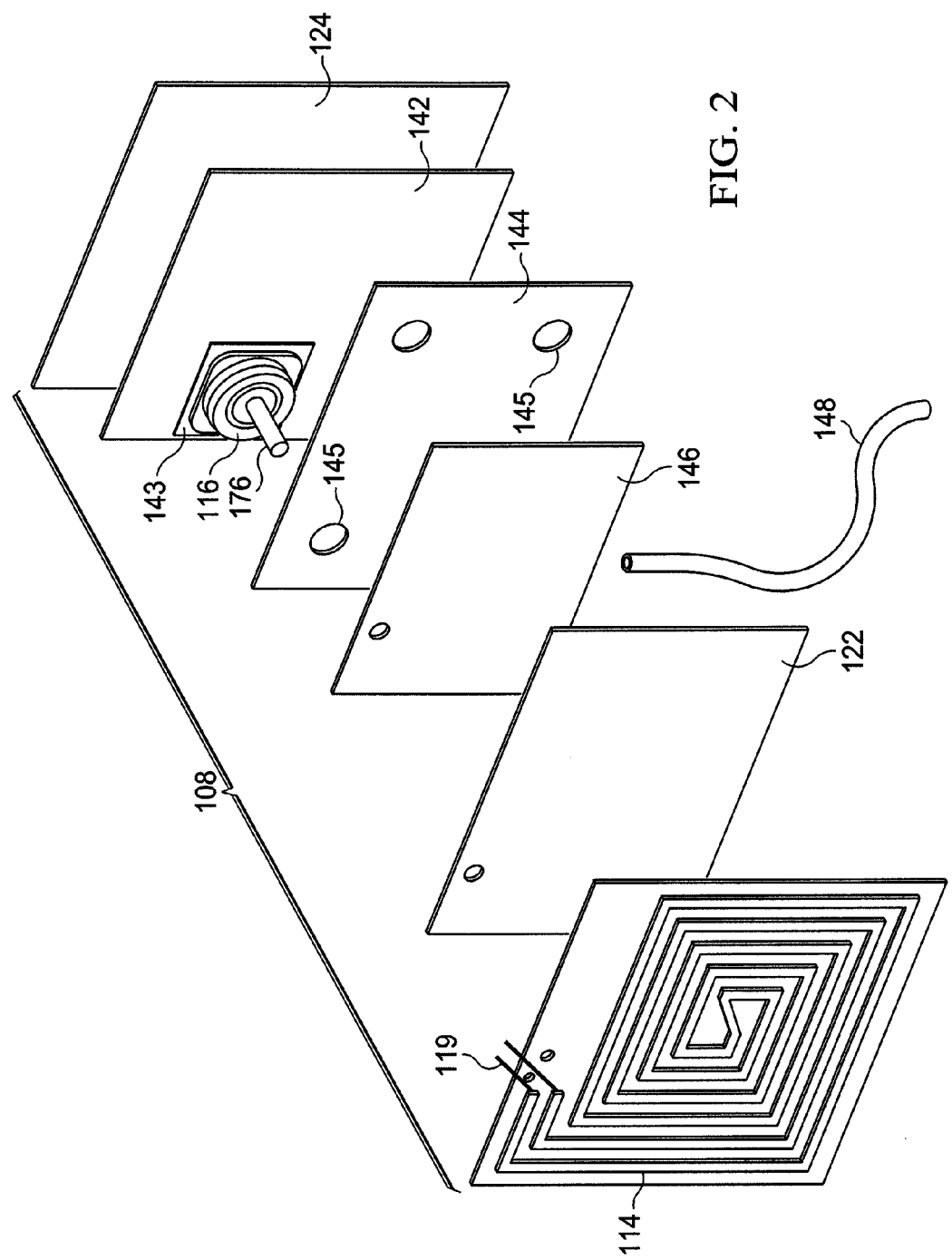
FIG. 2 is a schematic, exploded, perspective view of an illustrative embodiment of a wireless, reduced-pressure pump used as part of the system of FIG. 1.
Figure 4:
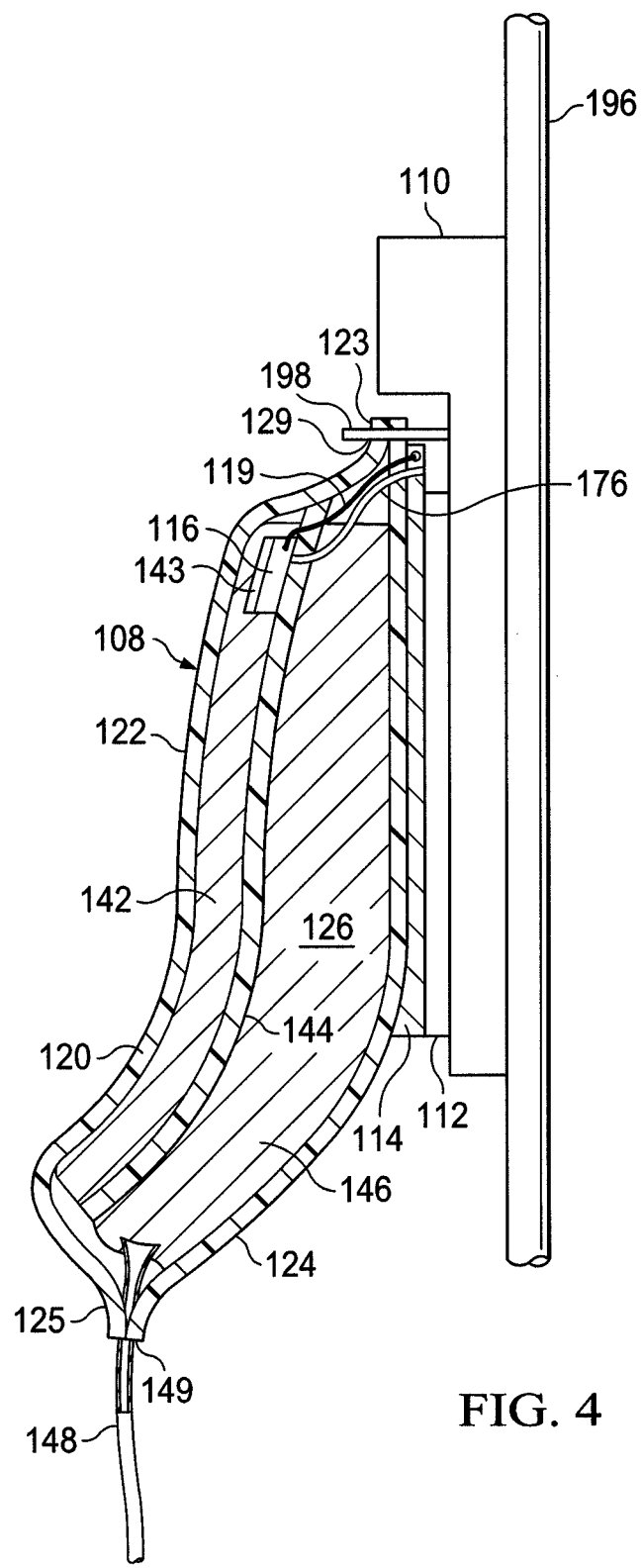
FIG. 4 is a schematic, partial cross-sectional view of an illustrative embodiment of a wireless, reduced-pressure pump.

Referring now primarily to FIGS. 2 and 4, the wireless, reduced-pressure pump 108 generates reduced pressure that is delivered to the tissue site 102. The wireless, reduced-pressure pump 108 receives and retains fluids from the tissue site 102. Reduced pressure generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, values of pressure stated herein are gauge pressures. The reduced pressure delivered may be constant or varied (patterned or random) and may be delivered continuously or intermittently. Consistent with the use herein, unless otherwise indicated, an increase in reduced pressure or vacuum pressure typically refers to a relative reduction in absolute pressure.

The wireless, reduced-pressure pump 108 provides the reduced pressure for the system 100. The wireless, reduced-pressure pump 108 may include a first distribution manifold 142, a diverter layer 144, and an absorbent layer 146. A vent 176 is used to fluidly couple an exhaust from the micro-pump device 116 to an exterior of the wireless, reduced-pressure pump 108. The first distribution manifold 142 functions to distribute reduced pressure generated by the micro-pump device 116. An air/liquid separator 143, e.g., a hydrophobic filter, may be placed between the micro-pump device 116 and the first distribution manifold 142 to prevent liquid from entering the micro-pump device 116. The absorbent layer 146 functions to receive and retain fluids from the tissue site 102. The absorbent layer 146 may be made from any material capable of absorbing liquid, such as exudate from the tissue site 102.

The absorbent layer 146 may be made from super absorbent fibers. The super absorbent fibers may retain or bond to the liquid in conjunction with a physical or chemical change to the fibers. In one non-limiting example, the super absorbent fiber may include the Super Absorbent Fiber (SAF) material from Technical Absorbents, Ltd. of Grimsby, United Kingdom. The absorbent layer 146 may be a sheet or mat of fibrous material in which the fibers absorb liquid from the tissue site 102. The structure of the absorbent layer 146 that contains the fibers may be either woven or non-woven. The fibers in the absorbent layer 146 may gel upon contact with the liquid, thereby trapping the liquid. Spaces or voids between the fibers may allow reduced pressure that is applied to the absorbent layer 146 to be transferred within and through the absorbent layer 146. In one illustrative embodiment, the fiber density of the fibers in the absorbent layer 146 may be approximately 1.4 grams per millimeter.

The diverter layer 144 is disposed adjacent to the absorbent layer 146 and the first distribution manifold 142. The diverter layer 144 is formed from a liquid impermeable material but contains a plurality of apertures 145. The plurality of apertures 145 allow reduced pressure from the micro-pump device 116 to be transmitted through the diverter layer 144 at desired locations. The diverter layer 144 helps control the pattern of reduced pressure as applied to the absorbent layer 146. The reduced pressure is distributed to the diverter layer 144 by the first distribution manifold 142. The apertures 145 may be arranged in a pattern for applying the reduced pressure to portions of the absorbent layer 146 to enhance the capability of the absorbent layer 146 to continue transferring reduced pressure to the tissue site 102 as the absorbent layer 146 absorbs more fluid from the tissue site 102.

The plurality of apertures 145 may be positioned in a pattern around a peripheral portion of the diverter layer 144 away from the center of the diverter layer 144 such that the reduced pressure is applied to the absorbent layer 146 away from a center region of the absorbent layer 146. The diverter layer 144 acts in conjunction with the first distribution manifold 142 to ensure that the absorption capabilities and absorption efficiency of the absorbent layer 146 are increased relative to an absorbent layer 146 that is not used in conjunction with a diverter layer 144. By providing better distribution of liquid throughout the absorbent layer 146, the diverter layer 144 also increases the effective capacity and treatment time of the wireless, reduced-pressure pump 108.

The diverter layer 144 may be made from any material that enhances the reduced pressure transmission and storage capabilities of an adjacent absorbent layer. For example, the diverter layer 144 may be made from a material that is substantially impermeable to liquid and gas and that diverts the reduced pressure to pass through apertures 145. Alternatively or in addition, the material from which the diverter layer 144 is made may have a predetermined moisture vapor transfer rate that is consistent with gas permeability. In either example, the diverter layer 144 may still include a pattern of apertures for transmitting a greater volume of liquid or gas than that permitted by a gas-permeable material not having apertures. It should be noted, however, that permeability of the diverter layer 144 to gas but not liquid may result in increased transmission of reduced pressure through the dressing while still directing liquid flow around or near the perimeter of the diverter layer 144.

The first distribution manifold 142, the diverter layer 144, and the absorbent layer 146 may be disposed within the pump pouch 120. The wireless, reduced-pressure pump 108 may also include the pressure sensing device 138, which is fluidly coupled to the reduced-pressure dressing 106 and in communication with the first processor 118 for sensing pressure. The reduced-pressure conduit 148 delivers fluids from the reduced-pressure dressing 106 to the wireless, reduced-pressure pump 108. In one illustrative embodiment, the reduced-pressure conduit 148 is disposed directly into the absorbent layer 146. In another illustrative embodiment, an interface (not shown) fluidly couples the reduced-pressure conduit 148 and the absorbent layer 146.

Referring now primarily to FIGS. 1 and 3, the reduced-pressure dressing 106 is disposed against the tissue site 102. The tissue site 102 may be, for example, the wound 104 through epidermis 156 and into subcutaneous tissue 158 or any other tissue site. The reduced-pressure dressing 106 may be any device for providing reduced pressure to the tissue site 102 and for receiving fluids from the tissue site 102. For example, the reduced-pressure dressing 106 may be formed with a foam member, a structure with a plurality of defined channels, a suction tube, or other device. In one illustrative embodiment, the reduced-pressure dressing 106 may include the interface distribution manifold 150 for placing proximate to the tissue site 102, a dressing sealing member 152, and a reduced-pressure interface 154.

A manifold is a substance or structure that is provided to assist in applying reduced pressure to, delivering fluids to, or removing fluids from a tissue site 102. The interface distribution manifold 150 typically includes a plurality of flow channels or pathways that distribute fluids provided to and removed from the tissue site 102 around the interface distribution manifold 150. In one illustrative embodiment, the flow channels or pathways are interconnected to improve distribution of fluids provided or removed from the tissue site 102. The interface distribution manifold 150 may be a biocompatible material that is capable of being placed in contact with the tissue site 102 and distributing reduced pressure to the tissue site 102. Examples of interface distribution manifolds may include without limitation the following: devices that have structural elements arranged to form flow channels, e.g., cellular foam, open-cell foam, porous tissue collections, liquids, gels, and foams that include, or cure to include, flow channels; foam; gauze; felted mat; or any other material suited to a particular biological application.

In one embodiment, the interface distribution manifold 150 is a porous foam and includes a plurality of interconnected cells or pores that act as flow channels. The porous foam may be a polyurethane, open-cell, reticulated foam such as GranuFoam® material available from Kinetic Concepts, Incorporated of San Antonio, Tex. In some situations, the interface distribution manifold 150 may also be used to distribute fluids such as medications, antibacterials, growth factors, and various solutions to the tissue site 102. Other layers may be included in or on the interface distribution manifold 150, such as absorptive materials, wicking materials, hydrophobic materials, and hydrophilic materials.

In one illustrative embodiment, the interface distribution manifold 150 in whole or in part may be constructed from bioresorbable materials that may remain in a patient's body following use of the reduced-pressure dressing 106. Suitable bioresorbable materials may include, without limitation, a polymeric blend of polylactic acid (PLA) and polyglycolic acid (PGA). The polymeric blend may also include without limitation polycarbonates, polyfumarates, and capralactones. The interface distribution manifold 150 may further serve as a scaffold for new cell-growth, or a scaffold material may be used in conjunction with the interface distribution manifold 150 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The interface distribution manifold 150 is covered by a dressing sealing member 152. The dressing sealing member 152 may be any material that provides a fluid seal. A fluid seal is a seal adequate to maintain reduced pressure at a desired site given the particular reduced-pressure source or subsystem involved. The dressing sealing member 152 may, for example, be an impermeable or semi-permeable, elastomeric material. Elastomeric materials have the properties of an elastomer. It generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional, specific examples of dressing sealing member materials include a silicone drape, 3M Tegaderm drape, polyurethane (PU) drape such as one available from Avery Dennison Corporation of Pasadena, Calif. The dressing sealing member 152 forms a sealed space 160 over the tissue site 102, which may or may contain the micro-pump device 116.

An attachment device 162 may be used to retain the dressing sealing member 152 against the patient's epidermis 156 or another layer, such as a gasket or additional sealing member. The attachment device 162 may take numerous forms. For example, the attachment device 162 may be a medically acceptable, pressure-sensitive adhesive that extends about a periphery or all of the dressing sealing member 152 or covers at least a potion of the dressing sealing member 152 on a patient-facing side over the epidermis 156.

The reduced-pressure interface 154 may be used to provide fluid communication between the reduced-pressure conduit 148 and the sealed space 160 of the reduced-pressure dressing 106. The reduced pressure may be delivered through the reduced-pressure conduit 148 to the reduced-pressure interface 154 and then to the sealed space 160. In one illustrative embodiment, the reduced-pressure interface 154 is a T.R.A.C.® Pad or Sensa T.R.A.C.® Pad available from KCI of San Antonio, Tex. The reduced-pressure conduit 148 may include the reduced-pressure lumen 164 and the pressure sensing lumen 166 formed as an integral conduit as shown in FIG. 1 or separately as shown in FIG. 3.

In one illustrative embodiment shown in FIG. 1, pressure sensing capability may be added to the reduced-pressure dressing 106 to function in addition to or in lieu of pressure sensing device 138. The reduced-pressure dressing 106 may include a second RFID antenna 168, a third processor 170, and a second pressure sensing device 172. The third processor 170 is coupled to the second RFID antenna 168 and to the second pressure sensing device 172. A vent passageway 174 provides fluid communication between the sealed space 160 and the second pressure sensing device 172. The third processor 170 and the second pressure sensing device 172 are operable to receive a pressure inquiry signal from the base unit 110 and respond with a pressure message signal indicative of the pressure in the sealed space 160.

In one illustrative embodiment, the wireless, reduced-pressure pump 108 is a wireless and passive (i.e., no battery) device. As such, the wireless, reduced-pressure pump 108 has no source of power other than power delivered through the first RFID antenna 114. In some embodiments, the wireless, reduced-pressure pump 108 may contain a capacitor for storing electrical energy. In another illustrative embodiment, the first power source 140 as shown in FIG. 3 may be provided to augment the power delivered through the first RFID antenna 114 or to operate the micro-pump device 116. The first power source 140 may be recharged by power from the first RFID antenna 114.

Figure 5:
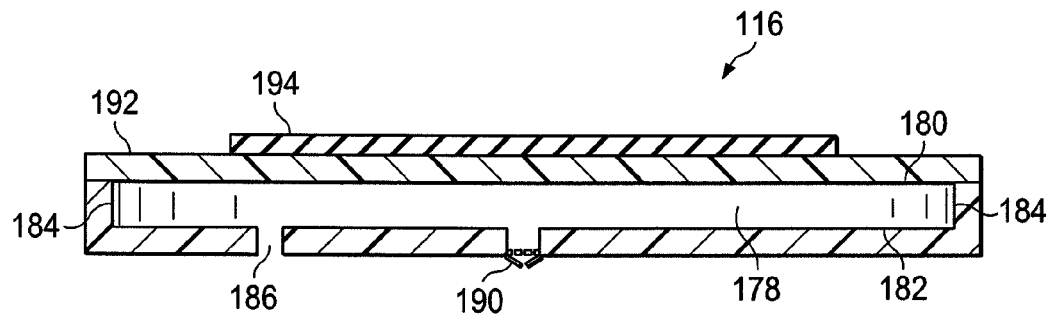
FIG. 5 is a schematic, cross section of one illustrative embodiment of a micro-pump device for use as part of a system for treating a tissue site with reduced pressure such as in FIG. 1.

The micro-pump device 116 may take numerous forms such as a piezoelectric pump, peristaltic pump, or other miniaturized pump. Referring now primarily to FIG. 5, an illustrative embodiment of a micro-pump device 116 that is suitable for use as an aspect of the wireless, reduced-pressure pump 108 is presented. The micro-pump device 116 includes a cavity 178 that is defined by a first end wall 180, a second end wall 182, and an annular side wall 184. The cavity 178 may be substantially circular in shape, but other shapes are possible, such as elliptical. In one illustrative embodiment, the cavity 178 may hold about 10 ml of fluid or may hold more or less.

The cavity 178 is provided with a nodal inlet 186, which may be valved or unvalved. The cavity 178 may also have a valved outlet 190. The first end wall 180 may be a disc 192. On the disc 192 is an actuator 194, such as a piezoelectric disc, magnetostrictive device, or solenoid actuated device. The actuator 194 is electrically coupled to a drive circuit, which is controlled by the processor. The drive circuit will apply an alternating electrical signal to the actuator 194 to induce an oscillation in the disc 192. The frequency of the oscillation can be adjusted to match the natural frequency of the chamber. The piezoelectric disc may be less than 1 mm in thickness and may be tuned to operate at more than 500 Hz, more than 10 kHz, or even higher than 20 kHz. Upon activation, the actuator 194 may vibrate in a direction substantially perpendicular to the plane of the cavity 178 as shown, thereby generating radial pressure oscillations within the fluid in the cavity 178. One or more micro-pump devices 116 may be used in parallel or series.

In one illustrative embodiment, the micro-pump device 116 has a fluid in the cavity 178 and has a substantially cylindrical shape that is bounded by the first end wall 180, second end wall 182, and side wall 184. At least two apertures, e.g., inlet 186 and outlet 190, are formed through the walls 180, 182, 184 forming the cavity 178. The cavity 178 has a radius, r, and a height, h, and $r/h > 1.2$ and $h^2/r > 4 \times 10^{-10}$ m. The actuator 194, which is a piezoelectric disc, creates an oscillatory motion of one of the end walls 180, 182 in a direction that is substantially perpendicular to the plane of the first end wall 180 and second end wall 182. Axial oscillations of the end walls 180, 182 drive radial oscillations of fluid pressure in the cavity 178 and allow for pumping that creates reduced pressure. The micro-pump device 116 is like an acoustic pump in that an acoustic resonance is set up within the cavity 178. The inlet 186 is used to pull fluids, and the outlet 190 is coupled to a vent, e.g., the vent 176 in FIG. 4, to discharge to an exterior. Other micro-pump devices may be used. The micro-pump device 116 may be the type of micro-pump shown in United States Patent Publication 2009/0240185 (application Ser. No. 12/398,904; filed 5 Mar. 2009), entitled, "Dressing and Method for Applying Reduced Pressure To and Collecting And Storing Fluid from a Tissue Site," which is incorporated herein for all purposes.

Referring now primarily to FIGS. 1-3, according to one illustrative embodiment, in operating the system 100, the reduced-pressure dressing 106 is applied to the tissue site 102. In particular, the interface distribution manifold 150 is disposed proximate to the tissue site 102. Then the interface distribution manifold 150 and the tissue site 102 are covered by the dressing sealing member 152 to create the sealed space 160. The attachment device 162 on the patient-facing side of the dressing sealing member 152 may help provide a fluid seal against a portion of the patient's epidermis 156. If not already installed, the reduced-pressure interface 154 may be applied, such as for example by cutting a small aperture in the dressing sealing member 152 and securing the reduced-pressure interface 154 over or through the aperture, or hole.

The wireless, reduced-pressure pump 108 is then provided and fluidly coupled by the reduced-pressure conduit 148 to the reduced-pressure interface 154. The wireless, reduced-pressure pump 108 is positioned such that the first RFID antenna 114 is placed within operating range of the base unit 110. In one illustrative embodiment, the first RFID antenna 114 is placed within a few millimeters of the RFID reader 112 of the base unit 110. In another illustrative embodiment, the first RFID antenna 114 may be placed as far away as ten meters from the RFID reader 112. Any distance within the given range may be readily used.

The base unit 110 is then activated by the user. The base unit 110 transmits a pump signal 137 to the wireless, reduced-pressure pump 108. The pump signal is received by the first RFID antenna 114, and the energy of the pump signal is delivered to the first processor 118. The first processor 118 provides energy to the micro-pump device 116. The micro-pump 116 creates reduced pressure that is delivered into the fluid reservoir 126 that is fluidly coupled to the reduced-pressure conduit 148. Thus, the reduced pressure is delivered to the reduced-pressure dressing 106 through the reduced-pressure conduit 148. Fluids from the tissue site 102 flow through the interface distribution manifold 150, reduced-pressure interface 154, and reduced-pressure conduit 148 into the fluid reservoir 126.

The pressure at the tissue site 102 may be monitored directly or indirectly using a pressure sensing device, such as pressure sensing device 138 of FIG. 3 or second pressure sensing device 172 of FIG. 1. In the first illustrative example, the second processor 128 and the RFID reader 112 of the base unit 110 may, separate from the pump signal or with the pump signal, transmit a pressure inquiry signal to the wireless, reduced-pressure pump 108. In response to the pressure inquiry signal, the first processor 118 and pressure sensing device 138 may prepare a pressure message signal to communicate a measurement of the pressure at the tissue site. Then, the pressure message signal may be used for further processing by the first processor 118 to develop a pump control signal for activating or deactivating the micro-pump 116 as may be needed. Alternatively or in addition, the first processor 118 may transmit the pressure message signal via the first RFID antenna 114 to the RFID reader 112. After arriving at the RFID reader 112, the pressure message signal is delivered to the second processor 128. Using the pressure message signal, the second processor 128 may prepare a pump control signal that is transmitted by the RFID reader 112 to the wireless, reduced-pressure pump 108 to deactivate or activate the micro-pump 116 as needed.

If, after providing an adequate interval, the pressure remains outside of a desired operating range, an alarm signal is created by the base unit 110 or by the wireless, reduced-pressure pump 108. The alarm may be a separate audible device, visual alarm, or the micro-pump 116 may function at a different frequency range, e.g., lower, to make an audible noise for the alarm.

With the second illustrative approach, the reduced-pressure dressing 106 includes the second RFID antenna 168 that is coupled to the third processor 170, which is coupled to the second pressure sensing device 172. The second pressure sensing device 172 experiences the pressure within the sealed space 160 via the vent passageway 174. The base unit 110 transmits a pressure inquiry signal to the second RFID antenna 168. In response, the second pressure sensing device 172 and third processor 170 produce a pressure message signal that is transmitted by the second RFID antenna 168 to the base unit 110. As before, the base unit 110 then produces a pump control signal that is transmitted to the wireless, reduced-pressure pump 108 to activate or deactivate the micro-pump 116. Alternatively, the third processor 170 may evaluate the pressure and prepare a pump control signal as part of a feedback or control loop.

Figure 6:
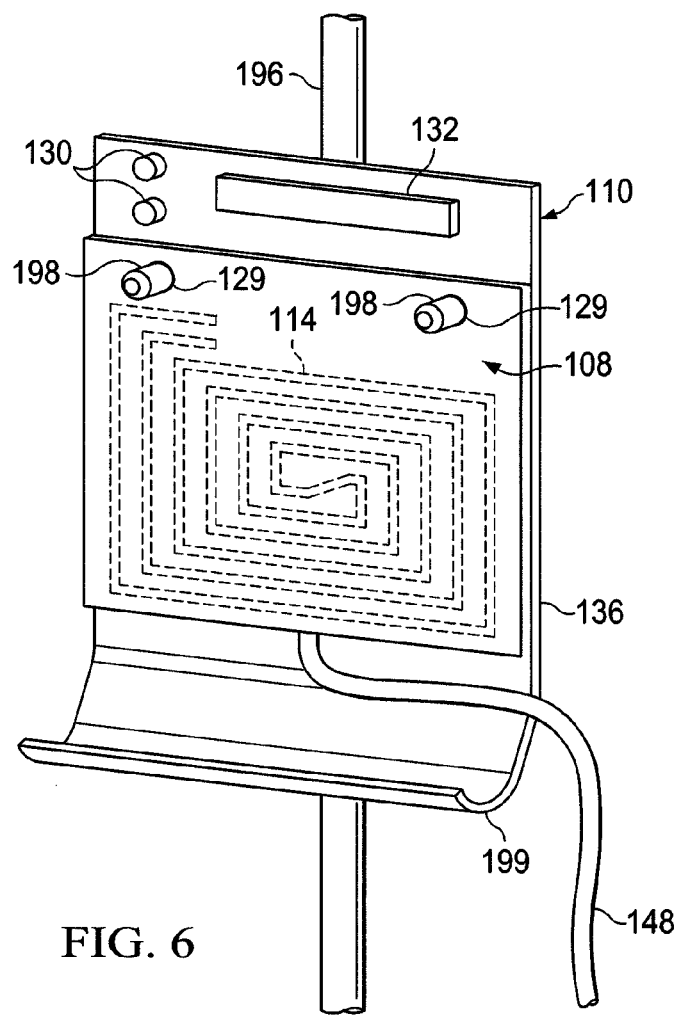
FIG. 6 is a schematic, perspective view of an illustrative embodiment of a wireless, reduced-pressure pump.

Referring now primarily to FIGS. 4 and 6, an illustrative embodiment of a wireless, reduced-pressure pump 108 is presented. In this illustrative embodiment, the wireless, reduced-pressure pump 108 may be a self-contained, disposable pouch design that may be removably secured to a base unit 110 on a pole 196. As previously presented, a pump pouch 120 is formed with a first pump-sealing member 122 and a second pump-sealing member 124. The perimeter of the pump pouch 120 may include a first flange 123 and a second flange 125. The pump pouch 120 may be divided or partitioned into numerous compartments if desired. For example, a compartment (not explicitly shown) may be formed that has the micro-pump 116 within the compartment and another compartment may formed that contains the absorbent layer 146.

The flanges 123, 125 on the illustrative embodiment of the pump pouch 120 may be formed by welding, bonding or otherwise attaching portions of the first pump-sealing member 122 and second pump-sealing member 124. The first flange 123 may include one or more apertures 129 for receiving one or more posts 198. The posts 198 secure the pump pouch 120 adjacent to the base unit 110. The reduced-pressure conduit 148 may enter through an aperture 149 in the second flange 125 that provides a sealed, interference fit or has a coupling that provides a sealed connection. Other connections may be used.

The first RFID antenna 114 may be placed closest to the base unit 110 such that the first RFID antenna 114 is immediately adjacent to RFID reader 112 of the base unit 110 as shown best in FIG. 4. In one non-limiting example, the first RFID antenna 114 is positioned two millimeters or one millimeter (1 mm) or less from the RFID reader 112. The RFID reader 112 and the first RFID antenna 114 may be substantially matched and aligned. In another illustrative embodiment, the wireless, reduced-pressure pump 108 may be attached to a post 198 with the first RFID antenna 114 facing outward towards a remotely located base unit 110 as suggested in FIG. 1. For example, the base unit 110 may be located at a central hub area where the wireless, reduced-pressure pump 108 is monitored and powered using the base unit 110, which may be as far away as ten meters or more.

Referring now primarily to FIG. 6, the base unit 110 may include the control panel 130 and one or more displays 132. The base unit 110 may include a base housing or base body 136. The base housing or body 136 may include a shelf portion 199 that may provide physical support to a portion of the wireless, reduced-pressure pump 108 when the wireless, reduced-pressure pump 108 fills with fluids from the tissue site 102. In this regard, it should be noted that the wireless, reduced-pressure pump 108 shown in FIG. 6 is shown before use. With the embodiments of FIGS. 4 and 6, when the wireless, reduced-pressure pump 108 has reached its capacity for holding fluids, the micro-pump 116 may be deactivated and the user may dispose of the entire wireless, reduced-pressure pump 108.

Figure 7:
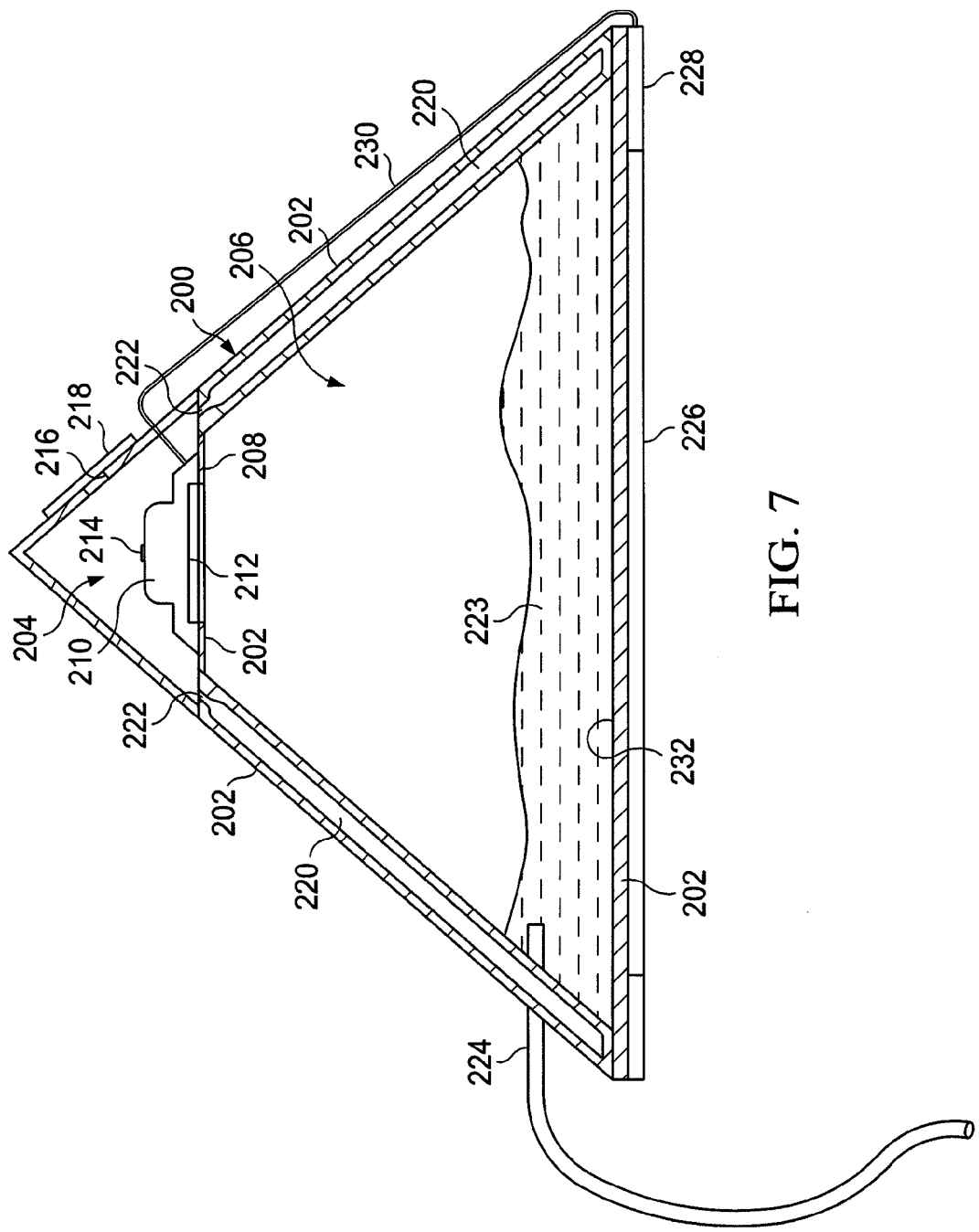
FIG. 7 is a schematic, cross section of another illustrative embodiment of a wireless, reduced-pressure pump.
Figure 8:
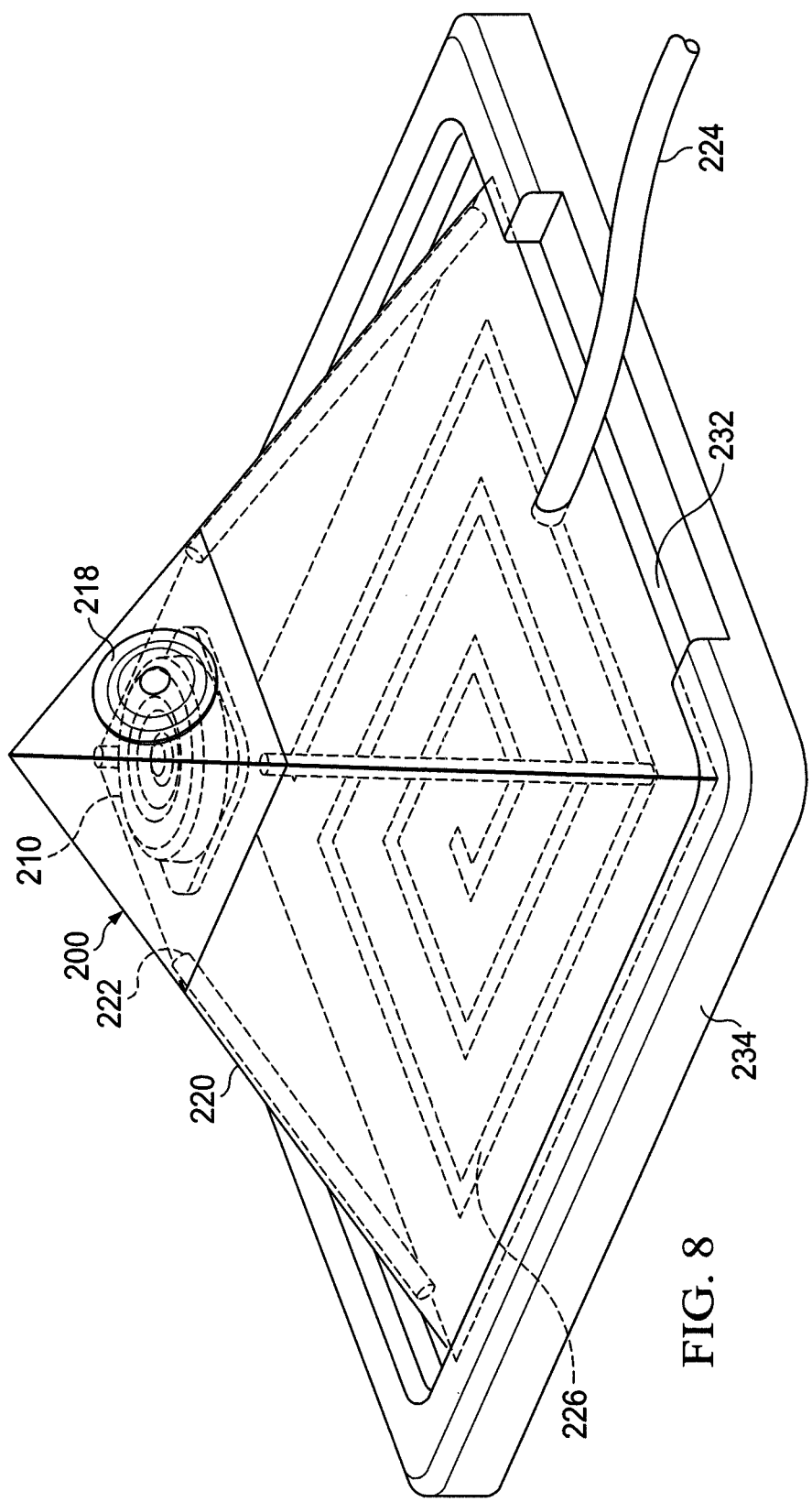
FIG. 8 is a schematic, perspective view of the wireless, reduced-pressure pump of FIG. 7.

Referring now primarily to FIGS. 7 and 8, another illustrative embodiment of a wireless, reduced-pressure pump 200 is presented. The wireless, reduced-pressure pump 200 may be used as part of a system for treating a tissue site, e.g., the system of FIG. 1. The wireless, reduced-pressure pump 200 includes a plurality of wall members 202 that form a first chamber 204 and a second chamber 206. One of the plurality of wall members 202 is a partitioning wall 208 that separates the first chamber 204 from the second chamber 206. A micro-pump 210, which is analogous to the micro-pump 116 of the previous figures, may be disposed within the first chamber 204. The micro-pump 116 is configured such that the inlet 212 that receives fluid (or said another way, discharges reduced pressure) is fluidly coupled to the second chamber 206. The micro-pump 210 has an outlet or vent 214 that is fluidly coupled to the first chamber 204. The micro-pump 210 vents positive pressure through outlet or vent 214 into the first chamber 204.

A portion of one of the plurality of wall members 202 that forms the first chamber 204 contains an aperture 216. An optional relief valve 218 is coupled to the aperture 216. The relief valve 218 is configured to allow pressure within the first chamber 204 to vent to an exterior of the wireless, reduced-pressure pump 200 when the pressure exceeds a first threshold pressure. At least a portion of the plurality of wall members 202 that make up the second chamber 206 includes an inflatable support member and typically a plurality of inflatable support members 220. While a plurality of inflatable support members 220 are presented, it should be understood that a single inflatable support member may be used create the second chamber 206.

The inflatable support members 220 are in fluid communication with the first chamber 204, such as through a plurality of apertures 222. Thus, the positive pressure within the first chamber 204 fills the plurality of inflatable support members 220. As the plurality of inflatable support members 220 are filled with sufficient fluid, the plurality of inflatable support members 220 gain relative rigidity that provides a structure that helps provide volume to the second chamber 206. Fluids 223 from a tissue site are received through a reduced-pressure conduit 224 into the volume of the second chamber 206. The wireless, reduced-pressure pump 200, which is shown in the shape of a pyramid, may be formed to take other shapes, e.g., a box, a cylinder, or any other shape.

As with the previous illustrative embodiments, the micro-pump 210 may be fully or partially powered by a pump signal delivered to a RFID antenna 226. The RFID antenna 226 is coupled to a first processor 228. The first processor 228 is electrically coupled to the micro-pump 210 by an electrical lead 230, which may be contained in one of the plurality of wall members 202 but is shown separately in FIG. 7. As shown in FIG. 8, a floor portion 232 of the plurality of wall members 202 may be contained within a platform member 234.

Referring now primarily to FIGS. 7 and 8, in operation according to one illustrative embodiment, the reduced-pressure conduit 224 is coupled to a reduced-pressure dressing, such as reduced-pressure dressing 106 of FIGS. 1 and 3. A base unit, e.g., base unit 110 of FIG. 1, is used to transmit a pump signal or a pump activation signal to the RFID antenna 226 of the wireless, reduced-pressure pump 200. The pump signal received by the RFID antenna 226 is delivered to the first processor 228. Power is delivered from the first processor 228 to the micro-pump 210 to energize micro-pump 210. As the micro-pump 210 is energized, reduced pressure is delivered into the second chamber 206 and positive pressure is delivered to the first chamber 204. As pressure builds in the first chamber 204, the pressure fills the plurality of inflatable support members 220 such that the wireless, reduced-pressure pump 200 changes from a deflated state to an inflated state. A spacer member (not shown) may cover the inlet 212 to avoid a vapor lock during start up before the inflatable support members 220 fill.

Once the inflatable support members 220 are inflated, the maximum volume is achieved for the second chamber 206. Meanwhile, the reduced pressure in the second chamber 206 is delivered to the reduced-pressure conduit 224. Fluids 223 (including liquids) are introduced into the second chamber 206.

While not explicitly shown, it should be understood that a reduced-pressure sensing device, e.g., analogous to pressure sensing device 138 in FIG. 3, may be incorporated into a portion of the second chamber 206 to measure pressure in the second chamber 206. Again, while not explicitly shown, it should be understood that a reduced-pressure sensing device, e.g., analogous to pressure sensing device 138 in FIG. 3, may be included in the reduced-pressure pump 200. The reduced-pressure conduit 224 may also have a pressure sensing lumen that is fluidly coupled to the reduced-pressure sensing device for measuring pressure at a distribution manifold. In both examples, the pressure sensing device is coupled to the first processor 228 to develop a pressure message signal. The pressure message signal may be supplied in response to a pressure inquiry signal from a base unit or self-generated by the first processor 228. The first processor 228 may use the pressure message signal to develop a pump control signal that is delivered to the micro-pump 210. Alternatively, the pressure message signal may be transmitted to the base unit where a processor in the base unit may develop a pump control signal similar to the embodiments previously presented.

In an alternative embodiment, the wireless, reduced-pressure pumps 108, 200 previously presented have, instead of having RFID antennas, electrical leads or sockets and plugs between the pumps and base. The electrical leads or sockets and plugs may readily plug into one another for communicating power and signals.

Figure 9:
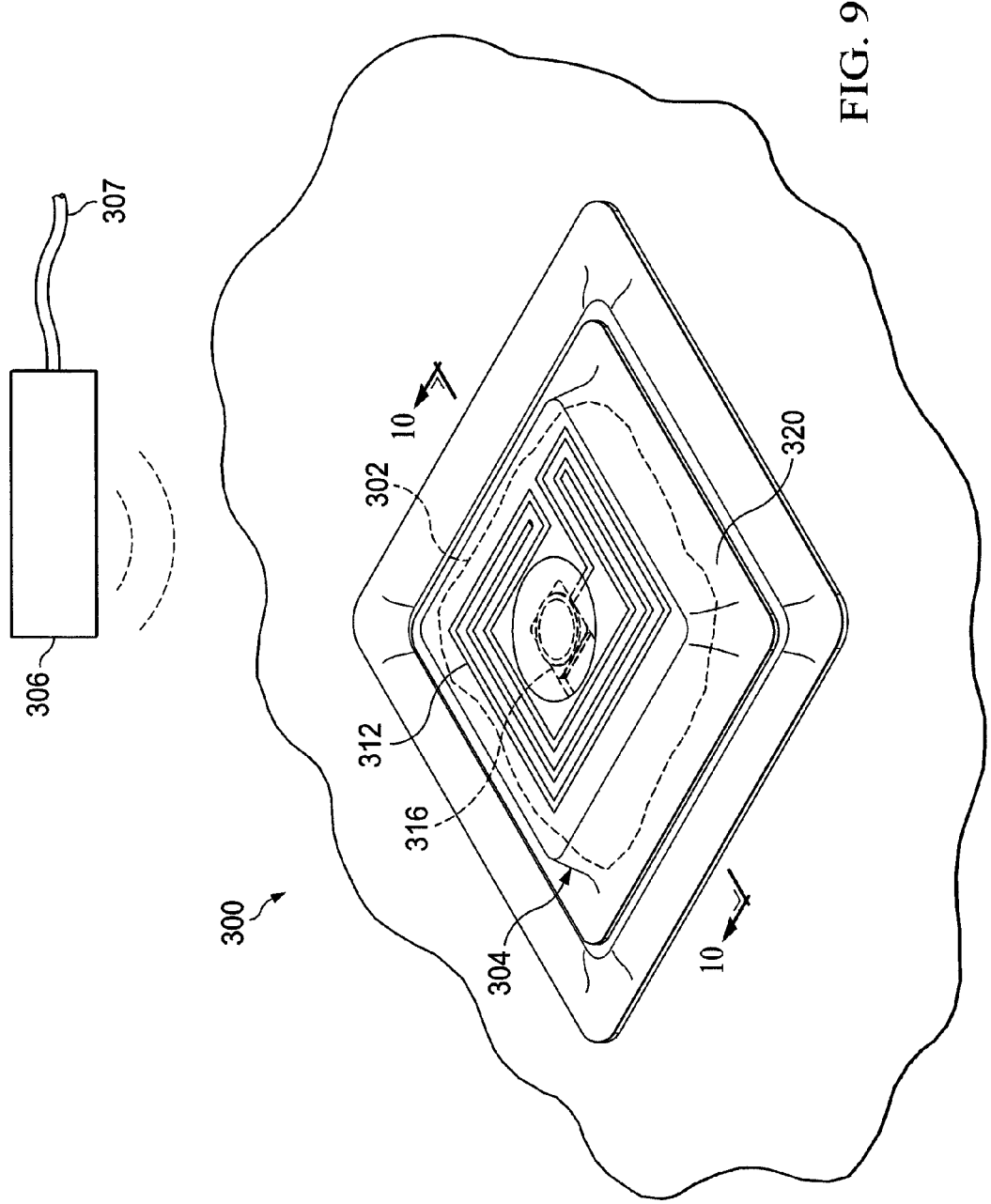
FIG. 9 is a schematic diagram, with a portion shown in perspective view, of an illustrative embodiment of a reduced-pressure system for treating a tissue site with reduced pressure.
Figure 10:
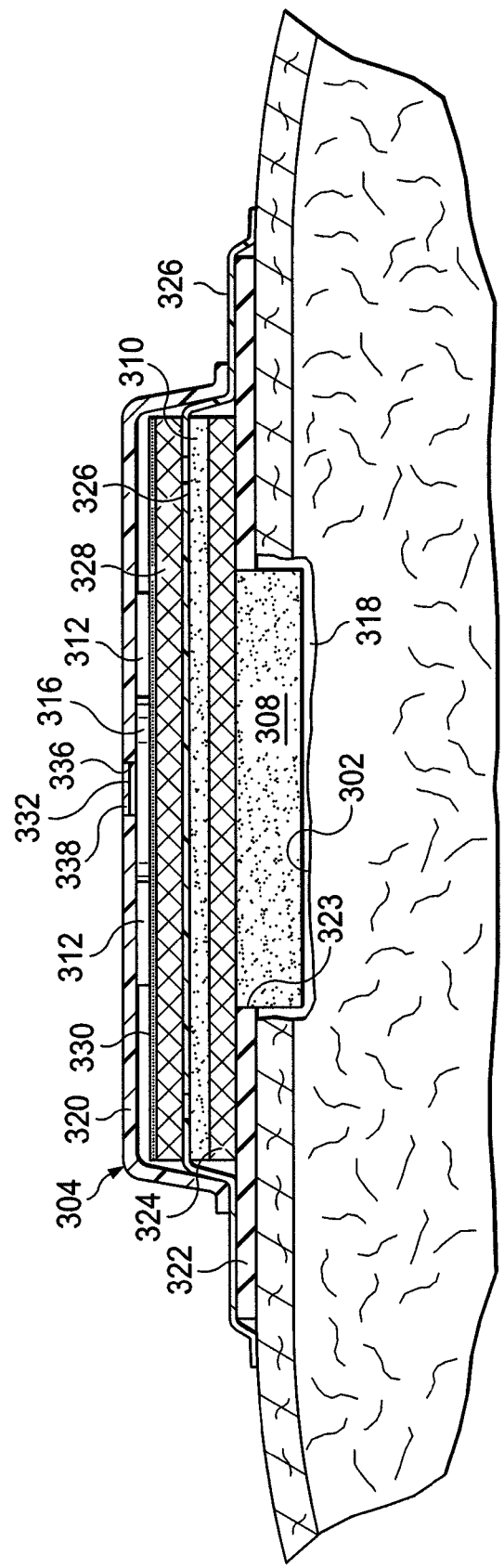
FIG. 10 is a schematic, cross section of the reduced-pressure dressing shown in FIG. 9 taken along line 10-10.
Figure 11:
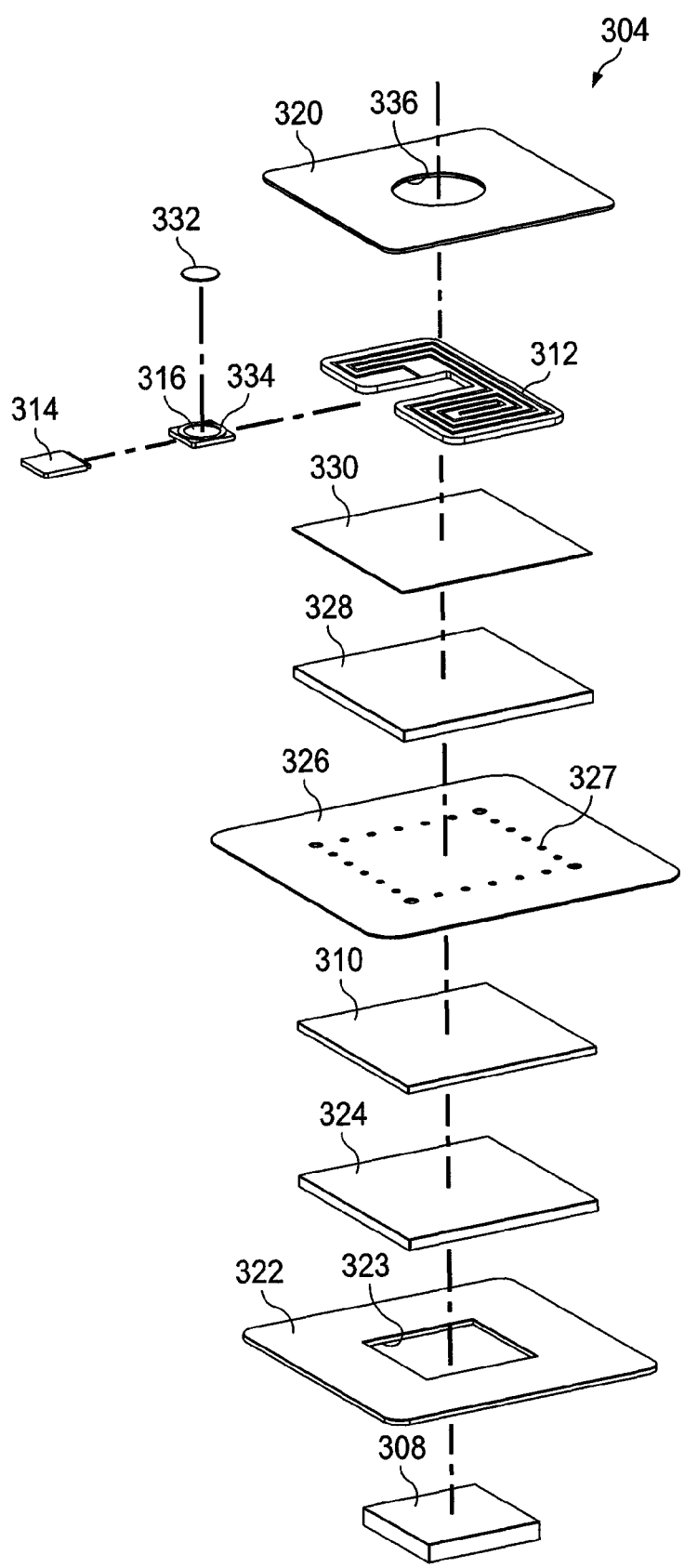
FIG. 11 is a schematic, exploded, perspective view of the reduced-pressure dressing of FIGS. 9-10.

Referring now primarily to FIGS. 9-11, an illustrative embodiment of a reduced-pressure system 300 for treating a tissue site 302 with reduced pressure is presented. The reduced-pressure system 300 includes a wireless, reduced-pressure dressing 304 and a base unit 306. The base unit 306 may include a power connector 307. The wireless, reduced-pressure dressing 304 is a self-contained, disposable dressing that receives power and control from the base unit 306. The base unit 306 may be substantially adjacent to the wireless, reduced-pressure dressing 304, e.g., within one or two millimeters, or up to 10 meters or more away or anywhere in between. In one embodiment, the micro-pump 316 may be separate from an absorbent layer or absorbent member 310, such that after use, the micro-pump 316 may be readily separated. The micro-pump 316 may then be reconditioned and reused.

The wireless, reduced-pressure dressing 304 includes an interface distribution manifold 308 that is placed proximate to the tissue site 302. The wireless, reduced-pressure dressing 304 may also include an absorbent layer 310, a RFID antenna 312, and a first processor 314. The RFID antenna 312 is electrically coupled to the first processor 314. The first processor 314 is electrically coupled to the micro-pump 316. The interface distribution manifold 308, absorbent layer 310, RFID antenna 312, first processor 314, and micro-pump 316 may all be retained in place and secured in a sealed space 318 by one or more sealing members, such as sealing member 320. Additional layers and components may be included in the wireless, reduced-pressure dressing 304.

The illustrative embodiment of FIGS. 9-11 includes additional layers and components. The additional layers and components may be arranged in different orders. A sealing layer 322 is used to seal the wireless, reduced-pressure dressing 304 around the tissue site 302. The sealing layer 322 is formed with an aperture 323 for providing fluid communication to the interface distribution manifold 308. A first internal distribution manifold 324 is positioned in fluid communication with the interface distribution manifold 308 and the tissue site 302. The absorbent layer 310 is positioned in fluid communication with the first internal distribution manifold 324, the interface distribution manifold 308, and a tissue site 302. A diverter layer 326 is positioned adjacent to the absorbent layer 310. A second internal distribution manifold 328 is positioned in fluid communication with the diverter layer 326. The diverter layer 326 is formed with a plurality of apertures 327 that may take numerous patterns and forms. The diverter layer 326 is shown in this particular illustrative embodiment with a plurality of apertures 327 forming a square pattern. The square pattern has corner apertures that are larger than the other apertures. A liquid-air separator 330 is positioned adjacent to the second internal distribution manifold 328.

The micro-pump 316, RFID antenna 312, and first processor 314 may be adjacent to the liquid-air separator 330. A charcoal filter 332 or other odor relieving device may be positioned over an outlet 334 of the micro-pump 316. The sealing member 320 is formed with an aperture 336 that allows the outlet 334 of the micro-pump 316 to exhaust to an exterior of the wireless, reduced-pressure dressing 304. The outlet 334 and aperture 336 together form a vent 338.

The micro-pump 316 may be a micro-pump that is small and light enough such that the integrated wireless, reduced-pressure dressing 304 is able to be maintained on the tissue site 302. Furthermore, the size and weight of the micro-pump 316 may be such that the integrated reduced-pressure dressing 304 does not pull or otherwise adversely affect the tissue site 302. In one illustrative embodiment, the micro-pump 316 may be a disk pump having a piezoelectric actuator similar to that previously described. Reference is also made to the pumps shown in United States Patent Publication 2009/0087323 and United States Patent Publication 2009/0240185, which are hereby incorporated by reference for all purposes. In an alternative embodiment, the micro-pump 316 may be a peristaltic pump that is used for pumping a variety of fluids. It should be understood that alternative pump technologies may be utilized and that rotary, linear, or other configurations of pumps may be utilized.

The micro-pump 316 creates sufficient reduced pressure to be therapeutic for wound therapy. In one illustrative embodiment, the micro-pump 316 has sufficient flow, reduced pressure, and operation life characteristics to enable continuous application of reduced pressure treatment. The flow may range between about 5-1000 ml/min and the reduced pressure may range between about −50 and −200 mm Hg (−6.6 to −26.6 kPa). It should be understood that alternative ranges may be utilized depending on the configuration of the integrated, wireless, reduced-pressure dressing 304, size of wound, or type of wound. In one illustrative embodiment, multiple pumps may be positioned in a single dressing to deliver increased flow rates or vacuum levels as required.

The micro-pump 316 is disposed within the dressing to avoid conduits and external canisters for collection of wound exudate. The micro-pump 316 includes the outlet 334 to release air or exhaust out of the reduced-pressure dressing 304. If the outlet 334 is used, the outlet 334 is in fluid communication with, or may be positioned within, the aperture 336 of the sealing member 320. Alternatively, the sealing member 320 may be sealed around an outlet port of the micro-pump 316 such that gas from the micro-pump 316 is able to exhaust directly through the aperture 336. In the illustrative embodiment in FIGS. 9-11, the outlet 334 of the micro-pump 316 is oriented in a direction away from the liquid-air separator 330 (or hydrophobic filter) to avoid adding air to the wireless, reduced-pressure dressing 304. The air exhausts through an aperture 336 in the sealing member 320, which may include a one-way valve. Alternatively, the air or another gas could be exhausted through a gas-permeable portion of the sealing member 320 as long as the ability of the sealing member 320 to maintain reduced pressure is not affected.

When the micro-pump 316 is a piezoelectric pump, the piezoelectric actuator associated with the micro-pump 316 may be driven at different frequencies to act as a buzzer or vibrating alert system at times. The alert system may alert a user to an alarm condition. For example, the alarm condition may indicate the presence of a leak in the dressing, a change in reduced pressure as measured by a sensor, that the dressing has absorbed a maximum capacity of liquid as may be indicated by an indicator, or that one or more layers are no longer manifolding reduced pressure efficiently.

Control electronics may be physically or functionally incorporated as part of the first processor 314. The control electronics may be utilized to control operation of the micro-pump 316. The control electronics may be analog or digital and be configured with a regulator to regulate speed or duty cycle at which the micro-pump 316 operates. Furthermore, the control electronics may be configured with a controller that receives sense signals from sensors or switches, e.g., a pressure sensing device (see 340 in FIG. 12). The sensors may be disposed throughout the wireless, reduced-pressure dressing 304 to sense parameters, such as pressure, temperature, moisture, chemistry, odor, or any other parameter that may be utilized in managing and controlling the micro-pump 316. The control electronics may include a computer processor or programmable gate array or other control device. It should be understood that the control electronics may include any form of digital or analog components to perform the functions described herein. The control electronics may be or include the first processor 314.

The control electronics may be arranged to monitor and provide an alarm for certain conditions, e.g., (i) low pressure, (ii) excessive leak, (iii) level of absorbent layer, and (iv) battery state (if included). Accordingly, the control electronics may include electronics that monitor each of the parameters and generate an alarm signal (e.g., high-pitched beep, vibration, or light) using a speaker, vibrator, or illumination device, such as a light emitting diode (LED). Thus, the control electronics may notify a medical professional, patient, or family member that a parameter is outside of a desired range. For example, if a pressure at the tissue site 302 is below a therapeutic level, a continuous tone may be generated. As another example, if the absorbent layer 310 is saturated, then continuous beeps may be generated. If the battery drops below a certain voltage level, then a different audible frequency may be generated or an LED may be activated. A variety of different alarm signals may be established to notify a medical professional to take a particular action.

The RFID antenna 312 is utilized to provide electric power to the micro-pump 316 and control electronics. A battery 342 may also be used to provide stored energy to augment power from the RFID antenna 312. The battery 342 may be any size and shape and may be of any material, such as polymer. The battery 342 may provide the entire needed power or a portion thereof. The battery 342 may be recharged by power from the RFID antenna 312.

In one illustrative embodiment, the battery 342 may be configured with a voltage level sensor that is monitored by the control electronics, and the control electronics may provide an alarm when a low power level is detected. The battery 342 may be directly connected to the micro-pump 316. Alternatively, the battery 342 may be connected to the control electronics or processor(s) that use power from the battery 342 to drive the micro-pump 316. The control electronics may provide continuous, modulated power, such as a pulsewidth modulated (PWM) signal, to drive the micro-pump 316.

The sealing layer 322 is adhered to or otherwise connected to the sealing member 320 that is used to drape or otherwise cover the components of the reduced-pressure dressing 304. The sealing layer 322 may include a medical-grade adhesive material or other sealing device that is strong enough to form a vacuum seal with epidermis around a wound of a patient. The sealing layer 322 may be a band that has an aperture 323 that is slightly larger than the geometric parameters of the liquid-air separator 330 or other layer so that the sealing member 320 contacts epidermis around the tissue site 302 of the patient. The sealing member 320 is impermeable to fluids, such as air and liquids.

In another illustrative embodiment, the sealing member 320 may be adhered to the diverter layer 326 and the diverter layer 326 adhered to the sealing member 320 to create an upper dressing portion and a lower dressing portion. The upper dressing portion may include the sealing member 320, the micro-pump 316 and related components, the liquid-air separator 330, the second internal distribution manifold 328, and the diverter layer 326. The lower dressing portion may include the absorbent layer 310, the first internal distribution manifold 324, the sealing layer 322, and the interface distribution manifold 308. The wireless, reduced-pressure dressing 304 may be configured to allow replacement of the lower dressing portion once the wireless, reduced-pressure dressing has absorbed a maximum capacity of fluid. The upper dressing portion may be reused after the lower dressing portion is replaced. This allows multiple uses of the micro-pump 316, while disposable portions of the dressing may be replaced. In another illustrative embodiment, the micro-pump 316, first processor 314, and RFID antenna 312 may be removed from the dressing for reuse and the remaining layers of the dressing replaced. In still another illustrative embodiment, only the absorbent layer 310 may be replaced. In yet another illustrative embodiment, only the absorbent layer 310 and the interface distribution manifold 308 may be replaced.

The charcoal filter 332 may be utilized in the wireless, reduced-pressure dressing 304 to reduce odors created by the tissue site 302 and dispersed from the wireless, reduced-pressure dressing 304. The charcoal filter 332 may be disposed above a valve or other output vent from the micro-pump 316 to filter exhaust from the micro-pump 316 prior to being released from the integrated reduced-pressure dressing 304. It should be understood that the charcoal filter 332 may be alternatively configured and disposed above or below the micro-pump 316. In another illustrative embodiment, rather than using a charcoal filter, charcoal may be integrated into any or all of the different layers utilized in the integrated reduced-pressure dressing 304.

According to one illustrative embodiment, in operation, the reduced-pressure system 300 of FIGS. 9-11, is applied by placing the interface distribution manifold 308 proximate to the tissue site 302. Placing the sealing layer 322 over the interface distribution manifold 308 such that the aperture 323 is over the interface distribution manifold 308. The first internal distribution manifold 324 is placed adjacent to the first interface distribution manifold 308 and possibly a portion of the sealing layer 322. The absorbent layer 310 is placed adjacent to the first internal distribution manifold 324. The diverter layer 326 may be placed over all the components thus presented. Then the second internal distribution manifold 328 may be placed adjacent to a portion of the diverter layer 326 along with the liquid-air separator 330. The micro-pump 316, RFID antenna 312, and first processor 314 may be applied. The components mentioned here may also be pre-assembled as a dressing stack.

The sealing member 320 is used to create a seal that forms a sealed space 318. The base unit 306 is used to transmit a pump signal as before to the RFID antenna 312 that is received by the first processor 314 and is used to provide power to the micro-pump 316. The first processor 314 may further include one or more capacitors for holding power or one or more batteries such as a rechargeable battery. The pump signal causes reduced pressure to be developed by the micro-pump 316. The reduced pressure is transmitted to the tissue site 302 to remove fluids or to provide reduced pressure therapy. The fluids removed from the tissue site 302 are transmitted within the reduced-pressure dressing 304 to the absorbent layer 310 where the fluids are retained or substantially retained. As will be described in connection with FIG. 12, a pressure sensing device may be included as part of the wireless, reduced-pressure dressing 304 to provide a pressure message signal to the base unit 306.

Figure 12:
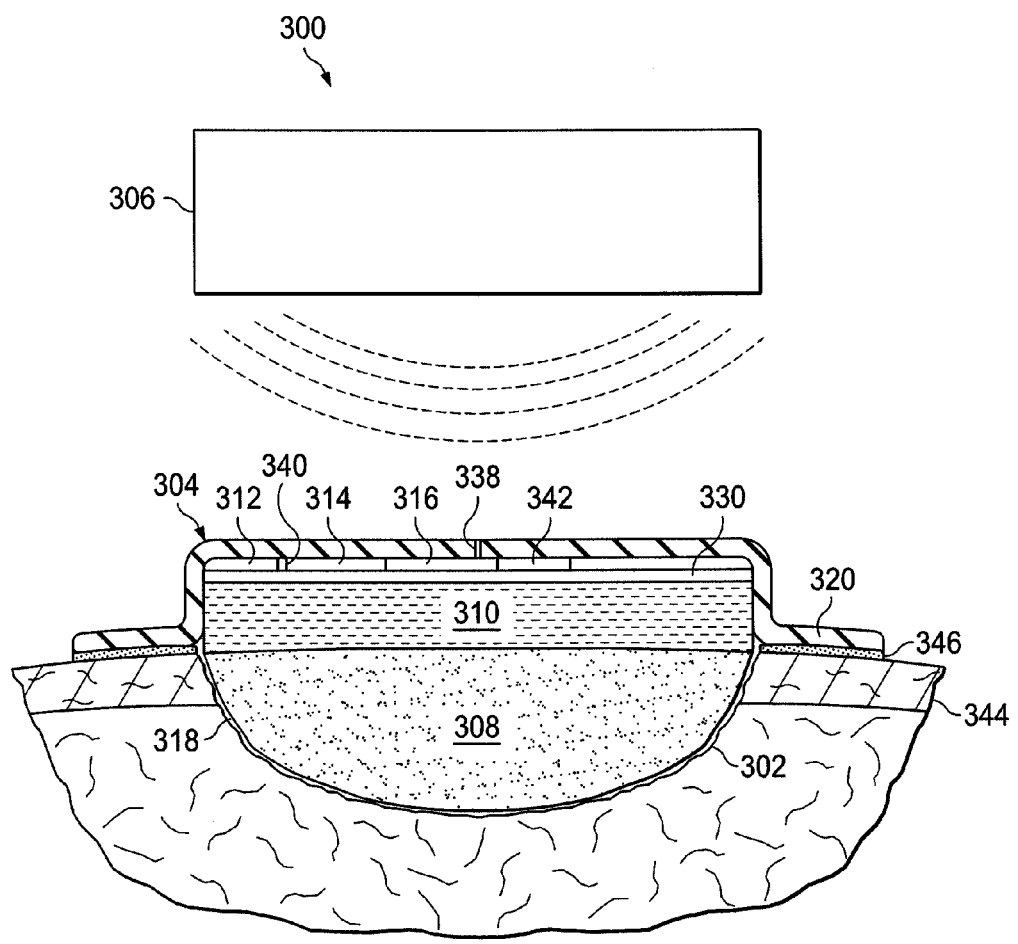
FIG. 12 is a schematic, cross section of an illustrative embodiment of a system for treating a tissue site with reduced pressure.

Referring now primarily to FIG. 12, another illustrative embodiment of a reduced-pressure system 300 is presented. As before, the reduced-pressure system 300 includes a wireless, reduced-pressure dressing 304 and a base unit 306. The reduced-pressure system 300 in FIG. 12 is analogous to the system presented in FIGS. 9-11, except that the wireless, reduced-pressure dressing 304 includes fewer components and includes the addition of a pressure sensing device 340 that is electrically coupled to the first processor 314. In addition, an optional battery 342 is included. The battery 342 may supplement power provided through the RFID antenna 312 or may be used as the primary power source and then recharged by the RFID antenna 312. The RFID antenna 312 receives power from the base unit 306. The sealing member 320 is shown secured to the epidermis 344 by an attachment device 346. Components included in the previous dressing of FIGS. 9-11 have been assigned the same reference numerals and are not necessarily discussed further here.

According to an illustrative embodiment, in operation, the reduced-pressure system 300 of FIG. 12 may be used by first applying the interface distribution manifold 308 adjacent to the tissue site 302. The absorbent layer 310 is placed in fluid communication with the interface distribution manifold 308. The liquid-air separator 330 may be placed over the absorbent layer 310. Then the RFID antenna 312, pressure sensing device 340, first processor 314, micro-pump 316, and battery 342 are disposed on the liquid-air separator 330. Alternatively, only some of the components, such as the micro-pump 316, may be adjacent to the liquid-air separator 330. The sealing member 320 is applied over the tissue site 302 to create a sealed space 318 and to cover all the aforementioned components. The previously mentioned components may be entirely or partially preassembled. The base unit 306 transmits a pump signal or pump activation signal to the reduced-pressure dressing 304 that activates the micro-pump 316. The micro-pump 316 removes air or other fluids from the sealed space 318 and thereby initiates treatment of the tissue site 302 with reduced pressure.

In addition to providing the pump activation signal or pump signal from the base unit 306 to the RFID antenna 312, the base unit 306 may also transmit a pressure inquiry signal. Upon receiving the pressure inquiry signal, the RFID antenna 312, the first processor 314, and the pressure sensing device 340 develop a pressure message signal that is transmitted by the RFID antenna to the RFID reader (not explicitly shown) of the base unit 306. The base unit 306 may include a processor (not explicitly shown) that receives the pressure message signal and develops a pump control signal to activate or deactivate the micro-pump 316. If the reduced pressure is in the desired therapy range, the micro-pump 316 may be deactivated. Similarly, if the pressure is too great on an absolute scale, the base unit 306 may transmit a pump signal that activates or continues the micro-pump 316 to produce more reduced pressure. If more than a sufficient elapsed time has passed without the desired pressure being reached, an alarm may be triggered by the base unit 306. The wireless, reduced-pressure dressing 304 may include a galvanic cell (not explicitly shown) to provide a full indication message signal when exudate or other body fluids electrically couple two electrodes. The full indication message signal would be transmitted with the RFID antenna 312 to the base unit 306 indicating that the dressing is full.

Figure 13:
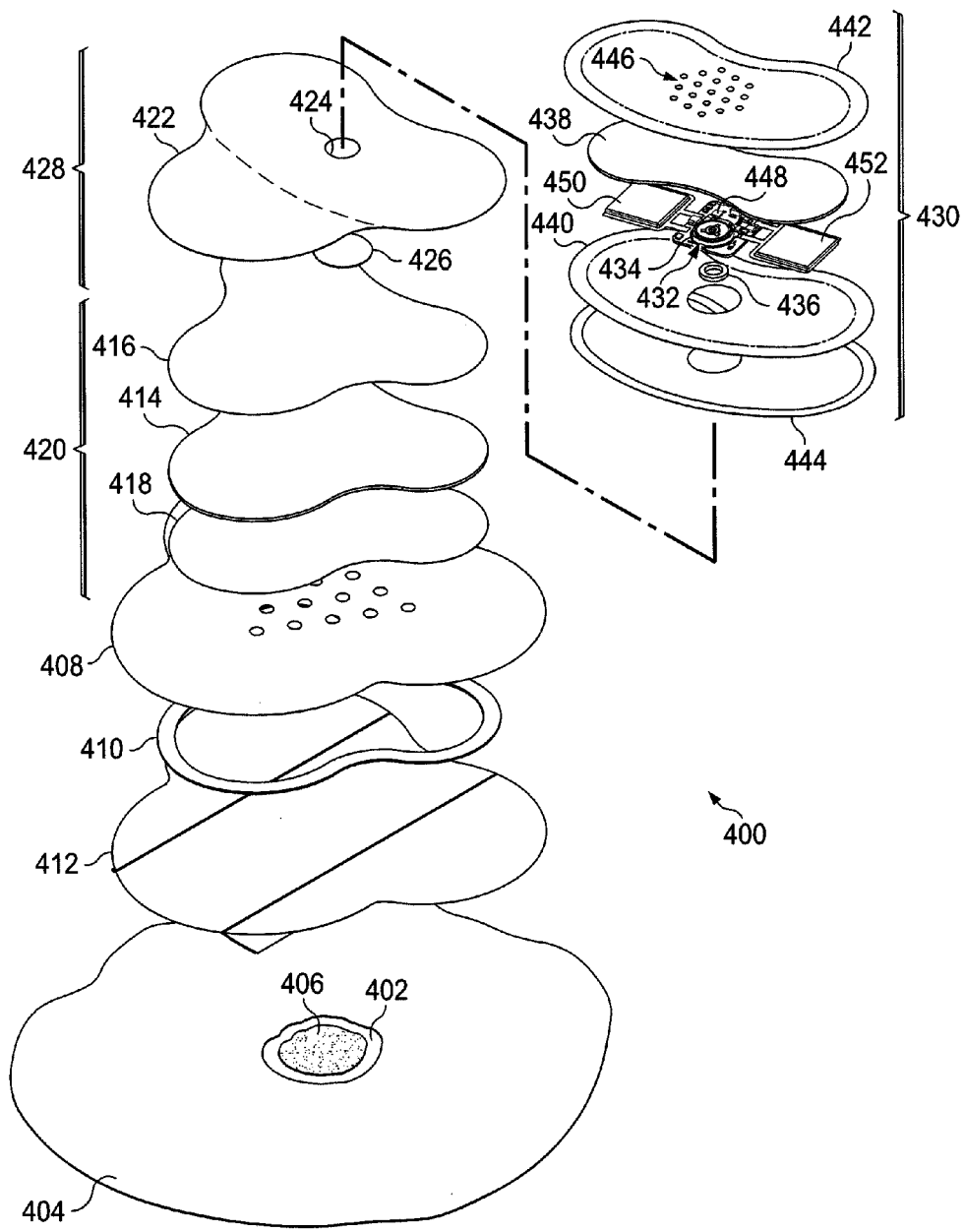
FIG. 13 is a schematic, exploded, perspective view of another illustrative embodiment of a reduced-pressure dressing.

Referring now primarily to FIG. 13, another illustrative embodiment of a reduced-pressure dressing 400 is presented that includes a wireless, reduced-pressure pump 430. The reduced-pressure dressing 400 is shown in an exploded view over a tissue site 402, such as a wound, on a patient 404. The reduced-pressure dressing 400 includes an interface distribution manifold 406, which is disposed proximate the tissue site 402. The interface distribution manifold 406 may be formed from any manifold material, such as a GranuFoam® material or any other manifold material previously mentioned.

The reduced-pressure dressing 400 further includes a lower drape or diverter 408. The lower drape 408 may be a polyethylene material having adhesive on a lower side (tissue-facing side) that adheres to the patient 404 surrounding the tissue site 402 being treated. The lower drape 408 includes apertures or perforations for communicating reduced pressure through the interface distribution manifold 406 to the tissue site 402 and drawing wound fluids (liquids or gases) from the tissue site 402. The lower drape 408 may also include a sealing ring 410 to provide additional adhesive strength to maintain the reduced pressure at a desired therapeutic level. A protective release liner 412 may initially cover the sealing ring 410. The protective release liner 412 is removed from the lower side of the lower drape 408 before the lower drape 408 is positioned on the patient 404.

The reduced-pressure dressing 400 includes an absorbent layer 414 that may be a non-woven fabric for absorbing the wound liquids being drawn through the apertures of the lower drape 408. The absorbent layer 414 is sandwiched between two wicking layers 416, 418 that wick and manifold the wound fluid to the absorbent layer 414. The dense side of the wicking layers 416, 418 face away from the absorbent layer 414. The wicking layers 416, 418 sandwich the absorbent layer 414 to form a fluid storage device 420.

The reduced-pressure dressing 400 further includes an upper drape 422 that may be a non-porous, occlusive barrier formed of polyethylene. The smooth side of the upper drape 422 faces the upper wicking layer 416. The upper drape 422 includes a aperture or opening 424. The aperture or opening 424 is covered by a hydrophobic filter 426 that separates air from liquid to contain the wound liquids or exudates within the absorbent layer 414. The hydrophobic filter 426 simultaneously permits the flow of gas from the absorbent layer 414 as a result of reduced pressure being applied to the hydrophobic filter 426. The upper drape 422 and the hydrophobic filter 426 comprise a top layer 428 of the reduced-pressure dressing 400 that covers the fluid storage device 420. All the elements of the dressing assembly described above except the release liner 412 may be referred to collectively as the "wound dressing" portion of the reduced-pressure dressing 400.

The reduced-pressure dressing 400 further includes the wireless, reduced-pressure pump, or pump portion 430. The pump portion 430 includes a micro-pump assembly 432 positioned on top of the upper drape 422 to provide a reduced pressure for drawing air through the hydrophobic filter 426, the fluid storage device 420, and the interface distribution manifold 406. The micro-pump assembly 432 includes a piezoelectric disc pump 434 that vibrates at a predetermined frequency to generate a desired reduced pressure at the input of the piezoelectric disc pump 434. The piezoelectric disc pump 434 may be analogous to micro-pump 316 of FIG. 12. The piezoelectric disc pump 434 of the micro-pump assembly 432 may not operate if any liquid drawn from the tissue site 402 into the absorbent layer 414 below the upper drape 422 enters the input port of the piezoelectric disc pump 434. The hydrophobic filter 426 prevents wound liquids or exudates from flowing into the piezoelectric disc pump 434 of the micro-pump assembly 432.

The reduced-pressure dressing 400 may also include a spacing ring or ring seal 436 positioned between the hydrophobic filter 426 and the inlet of the piezoelectric disc pump 434 to provide a cavity for air flow to the piezoelectric disc pump 434 of the micro-pump assembly 432. The micro-pump assembly 432 may be sandwiched between a first foam cushion 438 and second foam cushion 440. The micro-pump assembly 432, first cushion 438, and second cushion 440 are sandwiched between an outer ply 442 and an inner ply 444 and form a single composite package that is removably attached to the upper drape 422. The outer ply 442 includes apertures or perforations 446 that provide an exhaust path for the output of the micro-pump assembly 432.

The piezoelectric disc pump 434 or other micro-pump may be controlled by a first processor 448 and other control electronics. The piezoelectric disc pump 434 may be powered by a first power unit 450 and a second power unit 452. The power units 450, 452 may be batteries. In another illustrative, embodiment, the first power unit 450 or the second power unit 452 may comprise a RFID antenna that provides power to the first processor 448 and to the piezoelectric disc pump 434.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A system for treating a tissue site with reduced pressure, the system comprising:
   a reduced-pressure dressing for disposing proximate to the tissue site, the reduced-pressure dressing comprising an interface distribution manifold for placing proximate to the tissue site, a dressing sealing member, and a reduced-pressure interface;
   a wireless, reduced-pressure pump fluidly coupled to the reduced-pressure dressing, the wireless, reduced-pressure pump comprising:
      a RFID antenna,
      a first processor coupled to the RFID antenna,
      a micro-pump device coupled to the first processor for receiving power therefrom and developing reduced pressure, the micro-pump device comprising a piezoelectric pump,
      a first pump-sealing member and a second pump-sealing member, wherein the first pump-sealing member and the second pump-sealing member are at least partially coupled to form a pump pouch in which the micro-pump device is disposed,
a fluid reservoir fluidly coupled to the micro-pump device,
a first distribution manifold,
an absorbent layer, and
a diverter layer, wherein the first distribution manifold, the absorbent layer, and the diverter layer are disposed within the pump pouch formed by the first pump-sealing member and the second pump-sealing member;
a base unit having a RFID reader; and
wherein the RFID reader is configured to provide power to the RFID antenna such that the micro-pump device is powered.

2. The system of claim 1, wherein the wireless, reduced-pressure pump has no source of power other than the RFID antenna.

3. The system of claim 1, wherein the wireless, reduced-pressure pump further comprises a pressure sensing device fluidly coupled to the reduced-pressure dressing and to the first processor for sensing pressure at the tissue site.

4. The system of claim 1, wherein
the wireless, reduced-pressure pump further comprises a pressure sensing device coupled to the first processor,
the base unit comprises a second processor coupled to the RFID reader, and
the second processor and RFID reader are configured to transmit a pressure inquiry signal to the first processor of the wireless, reduced-pressure pump and to receive in response thereto a pressure message signal from the first processor.

5. The system of claim 1, wherein
the wireless, reduced-pressure pump further comprises a pressure sensing device coupled to the first processor,
the base unit comprises a second processor coupled to the RFID reader,
the second processor and RFID reader are configured to transmit a pressure inquiry signal to the first processor of the wireless, reduced-pressure pump and to receive in response thereto a pressure message signal from the first processor,
the first processor and pressure sensing device are configured to prepare the pressure message signal in response to the pressure inquiry signal,
the first processor and RFID antenna are configured to transmit the pressure message signal, and
the second processor is configured to receive the pressure message signal, prepare a control signal, and the second processor and RFID are configured to transmit the control signal to the wireless, reduced-pressure pump to provide a control signal for activating or deactivating the micro-pump device.

6. The system of claim 1, wherein
the wireless, reduced-pressure pump further comprises a pressure sensing device coupled to the first processor,
the pressure sensing device is operable to produce a pressure message signal, and
the first processor is operable to receive the pressure message signal and to produce a control signal to activate or deactivate the micro-pump device.

7. A method for treating a tissue site on a patient with reduced pressure, the method comprising:
placing a reduced-pressure dressing proximate to the tissue site, the reduced-pressure dressing comprising an interface distribution manifold for placing proximate to the tissue site, a dressing sealing member, and a reduced-pressure interface;
providing a wireless, reduced-pressure pump, wherein the wireless, reduced-pressure pump comprises:
a RFID antenna,
a first processor coupled to the RFID antenna,
a micro-pump device coupled to the first processor for receiving power therefrom and developing reduced pressure, the micro-pump device comprising a piezoelectric pump,
a first pump-sealing member and a second pump-sealing member, wherein the first pump-sealing member and the second pump-sealing member are at least partially coupled to form a pump pouch in which the micro-pump device is disposed,
a fluid reservoir fluidly coupled to the micro-pump device,
a first distribution manifold,
an absorbent layer, and
a diverter layer, wherein the first distribution manifold, the absorbent layer, and the diverter layer are disposed within the pump pouch formed by the first pump-sealing member and the second pump-sealing member;
fluidly coupling the wireless, reduced-pressure pump to the educed-pressure dressing;
providing a base unit having a RFID reader and a second processor; and
activating the base unit whereby the RFID reader and second processor transmit an activation signal to the wireless, reduced-pressure pump to activate the wireless, reduced-pressure pump.

8. The method of claim 7, wherein all the power required by the micro-pump device is delivered by the RFID reader.

9. The method of claim 7, further comprising the step of placing the RFID reader within five (5) centimeters of the RFID antenna of the wireless, reduced-pressure pump.

10. The method of claim 7,
wherein the wireless, reduced-pressure pump has no source of power other than the RFID antenna;
the wireless, reduced-pressure pump further comprising a pressure sensing device fluidly coupled to the reduced-pressure dressing and to the first processor for sensing pressure at the tissue site.

11. A wireless, reduced-pressure pump, the wireless, reduced-pressure pump comprising:
a RFID antenna;
a first processor coupled to the RFID antenna;
a micro-pump device coupled to the first processor for receiving power therefrom and developing reduced pressure, the micro-pump device comprising a piezoelectric pump;
a first pump-sealing member and a second pump-sealing member, wherein the first pump-sealing member and the second pump-sealing member are at least partially coupled to form a pump pouch in which the micro-pump device is disposed;
a first distribution manifold;
an absorbent layer; and
a diverter layer, wherein the first distribution manifold, the absorbent layer, and the diverter layer are disposed within the pump pouch formed by the first pump-sealing member and the second pump-sealing member;
wherein the wireless, reduced-pressure pump is adapted to be fluidly coupled to a reduced-pressure dressing, the reduced-pressure dressing comprising an interface distribution manifold for placing proximate to a tissue site, a dressing sealing member, and a reduced-pressure interface.

12. The wireless, reduced-pressure pump of claim 11, further comprising a fluid reservoir fluidly coupled to the micro-pump device.

13. The wireless, reduced-pressure pump of claim 11, wherein the wireless, reduced-pressure pump has no source of power other than the RFID antenna.

14. The wireless, reduced-pressure pump of claim 11, wherein the wireless, reduced-pressure pump further comprises a pressure sensing device fluidly coupled to the reduced-pressure dressing and to the first processor for sensing pressure at the tissue site.

15. The wireless, reduced-pressure pump of claim 11,
wherein the wireless, reduced-pressure pump further comprises a pressure sensing device coupled to the first processor;
further comprising a base unit that comprises a second processor coupled to a RFID reader; and
wherein the second processor and the RFID reader are configured to transmit a pressure inquiry signal to the first processor of the wireless, reduced-pressure pump and to receive in response thereto a pressure message signal from the first processor.

16. The wireless, reduced-pressure pump of claim 11,
wherein the wireless, reduced-pressure pump further comprises a pressure sensing device coupled to the first processor,
further comprising a base unit that comprises a second processor coupled to a RFID reader,
the second processor and the RFID reader are configured to transmit a pressure inquiry signal to the first processor of the wireless, reduced-pressure pump and to receive in response thereto a pressure message signal from the first processor,
the first processor and pressure sensing device are configured to prepare the pressure message signal in response to the pressure inquiry signal,
the first processor and the RFID antenna are configured to transmit the pressure message signal, and
the second processor is configured to receive the pressure message signal, prepare a control signal, and the second processor and the RFID reader are configured to transmit the control signal to the wireless, reduced-pressure pump to provide a control signal for activating or deactivating the micro-pump device.

17. The wireless, reduced-pressure pump of claim 11, wherein:
the wireless, reduced-pressure pump further comprises a pressure sensing device coupled to the first processor,
the pressure sensing device is operable to produce a pressure message signal, and
the first processor is operable to receive the pressure message signal and to produce a control signal to activate or deactivate the micro-pump device.

* * * * *